(12) United States Patent
Chapman et al.

(10) Patent No.: US 7,276,286 B2
(45) Date of Patent: Oct. 2, 2007

(54) SURFACES THAT RESIST THE ADSORPTION OF BIOLOGICAL SPECIES

(75) Inventors: Robert G. Chapman, Burlingame, CA (US); Emanuele Ostuni, Cambridge, MA (US); Michael N. Liang, Somerville, MA (US); Lin Yan, East Brunswick, NJ (US); George M. Whitesides, Newton, MA (US)

(73) Assignee: President & Fellows of Harvard College, Cambridge, MA (US)

( * ) Notice: Subject to any disclaimer, the term of this patent is extended or adjusted under 35 U.S.C. 154(b) by 20 days.

(21) Appl. No.: 09/907,551

(22) Filed: Jul. 17, 2001

(65) Prior Publication Data

US 2002/0102405 A1 Aug. 1, 2002

Related U.S. Application Data

(60) Provisional application No. 60/218,739, filed on Jul. 17, 2000.

(51) Int. Cl.
| | |
|---|---|
| *B32B 9/04* | (2006.01) |
| *B32B 15/04* | (2006.01) |
| *B32B 15/08* | (2006.01) |
| *B32B 27/34* | (2006.01) |

(52) U.S. Cl. ............... 428/411.1; 428/332; 428/336; 428/338; 428/339; 428/457; 428/458; 428/474.4

(58) Field of Classification Search ............ 428/332, 428/336, 338, 339, 457, 458, 474.4
See application file for complete search history.

(56) References Cited

U.S. PATENT DOCUMENTS

| | | | |
|---|---|---|---|
| 3,088,849 A | 5/1963 | Friedlander | |
| 3,909,469 A | 9/1975 | Miller | |
| 3,951,815 A | 4/1976 | Wrasidlo | |
| 3,983,299 A * | 9/1976 | Regnier | ............... 428/405 |
| 4,020,019 A | 4/1977 | Soldati et al. | |
| 4,082,884 A | 4/1978 | De Long | |
| 4,177,038 A | 12/1979 | Biebricher et al. | |
| 4,182,827 A | 1/1980 | Jones et al. | |
| 4,226,935 A | 10/1980 | Fusee | |
| 4,241,682 A | 12/1980 | Konstandt | |
| 4,355,105 A | 10/1982 | Lantero, Jr. | |
| RE31,126 E | 1/1983 | Dasher et al. | |
| 4,421,780 A | 12/1983 | Buzio et al. | |
| 4,485,227 A | 11/1984 | Fox | |
| 4,525,456 A | 6/1985 | Rohrbach | |
| 4,551,245 A | 11/1985 | Ramsden et al. | |
| 4,569,858 A | 2/1986 | Lim et al. | |
| 4,588,664 A | 5/1986 | Fielding et al. | |
| 4,659,572 A | 4/1987 | Murray | |
| 4,686,876 A | 8/1987 | Hume et al. | |
| 4,696,876 A | 9/1987 | Cael | |
| 4,767,619 A | 8/1988 | Murray | |
| 4,925,698 A | 5/1990 | Klausner et al. | |
| 4,940,737 A | 7/1990 | Braatz et al. | |
| 5,039,458 A | 8/1991 | Braatz et al. | |
| 5,252,743 A | 10/1993 | Barrett et al. | |
| 5,312,873 A | 5/1994 | Gregor et al. | |
| 5,403,750 A | 4/1995 | Braatz et al. | |
| 5,462,536 A | 10/1995 | Braatz et al. | |
| 5,472,861 A | 12/1995 | Lantero et al. | |
| 5,476,509 A | 12/1995 | Keogh et al. | |
| 5,512,131 A | 4/1996 | Kumar et al. | |
| 5,540,984 A | 7/1996 | Quincy, III et al. | |
| 5,624,711 A | 4/1997 | Sundberg et al. | |
| 5,650,234 A | 7/1997 | Dolence et al. | |
| 5,739,316 A | 4/1998 | Beer et al. | |
| 5,776,748 A | 7/1998 | Singhvi et al. | |

(Continued)

FOREIGN PATENT DOCUMENTS

| | | |
|---|---|---|
| EP | 1110964 A1 | 6/2001 |
| JP | 10176021 A | 6/1998 |
| WO | WO 94/11411 A1 | 5/1994 |
| WO | WO 96/29629 A2 | 9/1996 |
| WO | WO 97/20639 A1 | 6/1997 |
| WO | WO 98/09735 A1 | 3/1998 |
| WO | WO 98/17407 A1 | 4/1998 |
| WO | WO 99/05509 A1 | 2/1999 |
| WO | WO 99/26729 A1 | 6/1999 |
| WO | WO 99/61531 | * 12/1999 |
| WO | WO 99/61531 A1 | 12/1999 |
| WO | WO 02/06407 A2 | 1/2002 |

OTHER PUBLICATIONS

"Fabrication of Gold Nanostructures by Lithography With Self-Assembled Monolayers," IBM Technical Disclosure Bulletin, 39 (12):235-238 (1996).

Brockman, J. et al., "A Multistep Chemical Modification Procedure to Create DNA Arrays on Gold Surfaces for the Study of Protein-DNA Interactions with Surface Plasmon Resonance Imaging," J. Am. Chem. Soc., 1999, 121, 8044-8051.

(Continued)

*Primary Examiner*—Sheeba Ahmed
(74) *Attorney, Agent, or Firm*—Wolf, Greenfield & Sacks, P.C.

(57) ABSTRACT

The present invention provides articles resistant to the adsorption of proteins, cells and bacteria. The articles can either have a chemical chain bonded thereon where the chemical chain can comprise a terminal group free of a hydrogen bond donor or where a hydrogen bond donor is sufficiently buried such that an exposed surface of the article including the chemical chain is free of a hydrogen bond donor. The chemical chain, or plurality of chemical chains, can comprise a monolayer such as a self-assembled monolayer (SAM) which can be homogeneous (one type of SAM) or mixed, i.e. or more different types of SAMs. Other more specific examples of chemical chains are provided. The plurality of chemical chains can comprise a polymer such as a polyamine. In many aspects, the plurality of chemical chains is sufficiently free of cross-linking or branching. The present invention also provides an article capable of specific binding of a desired biomolecule while preventing non-specific binding of biomolecules.

45 Claims, 12 Drawing Sheets

U.S. PATENT DOCUMENTS

| | | | |
|---|---|---|---|
| 5,804,318 A * | 9/1998 | Pinchuk et al. ............. 428/421 | |
| 5,834,583 A | 11/1998 | Hancock et al. | |
| 5,888,405 A | 3/1999 | McNeel et al. | |
| 5,889,073 A | 3/1999 | Zhang et al. | |
| 5,922,214 A | 7/1999 | Liu et al. | |
| 5,990,043 A | 11/1999 | Kugler et al. | |
| 5,993,890 A | 11/1999 | Marchant et al. | |
| 6,013,855 A | 1/2000 | McPherson et al. | |
| 6,030,971 A | 2/2000 | Whittemore et al. | |
| 6,054,504 A * | 4/2000 | Dalla Riva Toma ........ 523/122 | |

OTHER PUBLICATIONS

Chapman, R. et al., "Polymeric Thin Films that Resist the Adsorption of Proteins and the Adhesion of Bacteria," *Langmuir*, 2001, 17, 1225-1233.

Chechik, V., et al., "Reactions and Reactivity in Self-Assembled Monolayers" *Adv. Mater.*, 12 (16):1161-1171 (2000).

Holmlin, R. et al., "Zwitterionic SAMs that Resist Nonspecific Adsorption of Protein from Aqueous Buffer," *Langmuir*, 2001, 17, 2841-2850.

Huck, W. et al. "Synthesis of Geometrically Well Defined, Molecularly Thin Polymer Films," *Angew. Chem. Int. Ed.*, 2000, 39, No. 6, pp. 1058-1061.

Ishihara, K., "Prevention of Protein Adsorption by the Phospholipid Polymers," *Polym. Mater. Sci. Eng.*, 1997, 77, 574-575.

Maeda, H. et al., "Electrochemical Coating with Poly(phenylene oxide) Films Bearing Oligoether Groups as a Tool for Elimination of Protein Adsorption to Electrode Surfaces," *Analytical Sciences*, Jul. 1999, vol. 15, 633-639.

Ostuni, E. et al., "Selective Deposition of Proteins and Cells in Arrays of Microwells," *Langmuir*, 2001, 17, 2828-2834.

Ostuni, E. et al., "The Interaction of Proteins and Cells with Self-Assembled Monolayers of Alkanethiolates on Gold and Silver," *Colloids and Surfaces B: Biointerfaces*, 15 (1999) 3-30.

Sekar, M et al., "Multifunctional Monolayer Assemblies for Reversible Direct Fluorescence Transduction of Protein-Ligand Interactions at Surfaces," *J. Am. Chem. Soc.*, 1999, 121, 5135-5141.

Zhang, S. et al., "Biological Surface Engineering: A Simple System for Cell Pattern Formation," *Biomaterials*, 20 (1999) 1213-1220.

Yan, et al., Patterning Thin Films of Poly(ethylene imine) on a Reactive SAM Using Microcontact Printing, Langmuir, Jan. 14, 1999, pp. 1208-1214, vol. 15, No. 4, American Chemical Society.

Ostuni, et al., The interaction of proteins and cells with self-assembled monolayers of alkanethiolates on gold and silver, Colloids and Surfaces B: Biointerfaces 15, 1999, pp. 3-30. Elsevier Science B.V.

Chapman, et al., Preparation of Mixed Self-Assembled Monolayers (SAMs) That Resist Adsorption of Proteins Using the Reaction of Amines with a SAM That Presents Interchain Carboxylic Anhydride Groups, Jul. 25, 2000. pp. 6927-6936, vol. 16. No. 17, American Chemical Society.

Chapman, et al., Polymeric Thin Films That Resist the Adsorption of Proteins and the Adhesion of Bacteria, Jan. 26, 2001, pp. 1225-1233, vol. 17, No. 4, American Chemical Society.

Chapman, et al., Surveying for Surfaces that Resist the Adsorption of Proteins, J. Am Chem Soc. Aug. 12, 2000, vol. 122, No. 34.

\* cited by examiner

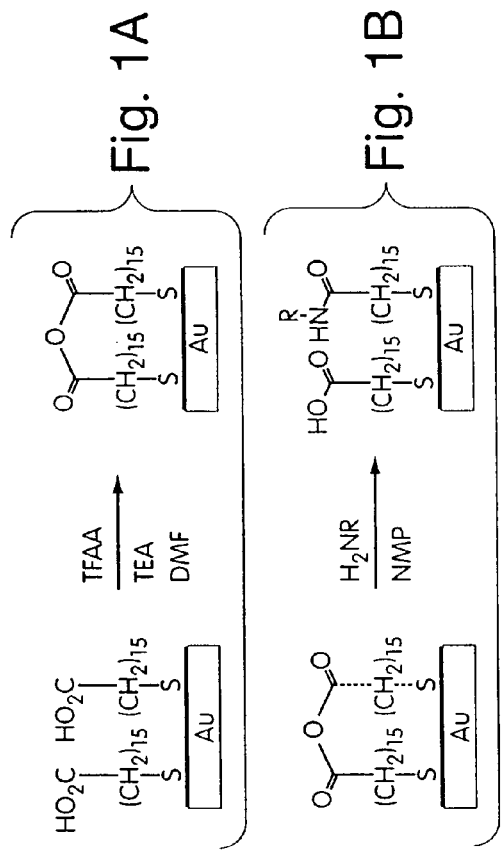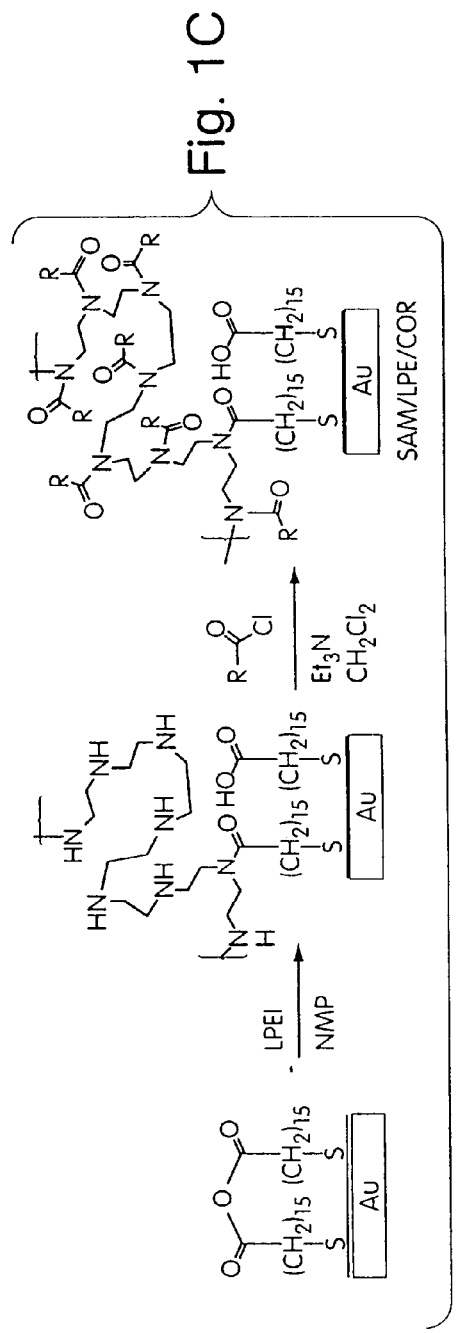

SURFACES THAT RESIST THE ADSORPTION OF BIOLOGICAL SPECIES

RELATED APPLICATIONS

This non-provisional application claims the benefit under Title 35, U.S.C. §119(e) of co-pending U.S. provisional application Ser. No. 60/218,739, filed Jul. 17, 2000, incorporated herein by reference.

GOVERNMENT FUNDING

This invention was sponsored by the National Institutes of Health Grant Number GM30367. The government has certain rights in the invention.

FIELD OF INVENTION

The present invention relates to articles having substrate surfaces covalently bonded to compositions and polymers which are capable of rendering the article resistant to the adsorption of proteins, cells, and/or bacteria. The present invention also relates to substrate surfaces covalently bonded to compositions capable of binding specifically to biomolecules, cells and bacteria.

BACKGROUND OF THE INVENTION

Continuous efforts are being made to develop new and improved biocompatible materials for the manufacture of medical devices, medical articles or materials used for various medical treatments. Generally, biocompatibility is achieved by designing materials that resist the adsorption and deposition of proteins, cells, and/or bacteria. The applications for such biocompatible materials are numerous, and include materials for prostheses, tissue substitutes, wound dressings, materials for the transfer of drugs and vaccines, and sensing devices. These materials can also be useful to prevent fouling, such as in watercraft devices that tend to accumulate bacteria, mold or marine organisms.

Surfaces including a low density distribution of high molecular weight ethylene glycol units have been reported to be effective for resisting the adsorption of proteins. Du et al. describes grafting poly(ethylene glycol) on lipid surfaces to inhibit the adsorption of proteins and cells (Biochimica et Biophysica Acta, Vol. 1326, pp. 236-248, 1997). Substrate surfaces have also been derivatized with poly(ethylene glycol) units via self-assembled monolayers. Harder et al. describes silver and gold surfaces bonded to n-alkanethiolates derivatized with oligo(ethylene glycol)-terminated units (J. Phys. Chem. B, Vol. 102, pp. 426-436, 1998). Prime et al. describes mixed self-assembled monolayers on gold in which oligo(ethylene oxide)-grafted alkanethiolate chains are mixed with alkanethiolate chains (J. Am. Chem. Soc., Vol. 115, pp. 10714-10721, 1993).

Cunliffe et al. describes silica surfaces derivatized with poly(ethylene oxide) that exhibit resistance to the adsorption of bacteria (Applied and Environmental Microbiology, Vol. 65 (11), pp. 4995-5002, November 1999).

Oligo(ethylene glycol) units are disadvantageous, however, because these units can be susceptible to autoxidation. Thus, there is a need for surfaces derivatized with compositions other than ethylene glycol units. Van der Heiden describes a poly(ether urethane) surface derivatized with phosphorylcholine to produce a passivated surface towards protein adsorption and platelet adhesion (J. Biomed. Mater. Res. Vol. 40, pp. 195-203, 1998). Deng et al. describes a surface containing self-assembled monolayers of tri(propylene sulfoxide) groups, which can be mixed with alkane terminated chains, to prepare surfaces which resist the adsorption of proteins (J. Am. Chem. Soc., Vol. 118, pp. 5136-5137, 1996).

Certain polymers also display protein-resistant properties. U.S. Pat. No. 4,241,682 (Konstandt) describes the use of a polymeric solution which can be coated onto a painted surface to increase the life of the painted surface. The solution includes a mixture of polyethylenimine and a hydrophilic acrylic polymer. U.S. Pat. No. 5,312,873 describes polymers having surface nitrile groups which are converted to amides, resulting in a membrane that resists absorptive fouling. U.S. Pat. No. 4,925,698 (Klausner et al.) describes a chemical modification of polymeric surfaces that renders the polymers more resistant to the deposition of proteins. In particular, the chemical modification involves acylation.

As there is no material that completely resists the adsorption of proteins, cells and bacteria, there remains a need to develop new materials.

SUMMARY OF THE INVENTION

Certain aspects of the present invention feature articles resistant to the adsorption of biological species, such as proteins, cells and/or bacteria through the provision of novel surface-bound compositions and mixtures of these compositions.

One aspect of the present invention provides an article, comprising a substrate having covalently bonded thereon a chemical chain, the chain comprising a terminal group comprising the structure:

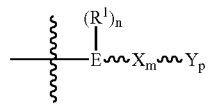

wherein the terminal group is hydrophilic. E is selected from the group consisting of nitrogen, oxygen, phosphorus and sulfur. X is an organic substituent and m is an integer less than or equal to 3. Y is selected from the group consisting of amides, amide derivatives, amines, amine derivatives, cyclic ethers, sugar derivatives, amino acids, amino acid derivatives, and multiple nitrites and p is an integer greater than 0; X and Y are both free of a hydrogen-bond donor. $R^1$ is selected from the group consisting of hydrogen, a $C_1$-$C_6$ alkyl and an aryl, and n is an integer less than or equal to 2. ∿∿∿represents one or more single bonds, a double bond, or any combination thereof. Optionally $R^1$ can bond to X or Y to form a cyclic structure.

Another aspect of the present invention provides an article, comprising a substrate having covalently bonded thereon a monolayer of chemical chains. At least 25% of the chains of the monolayer are terminated with a hydrophilic group free of a hydrogen-bond donor. The hydrophilic group is selected from the group consisting of amides, amide derivatives, amines, amine derivatives, cyclic ethers, sugar derivatives, amino acids, amino acid derivatives, and multiple nitrites.

Another aspect of the present invention provides an article comprising a substrate having a chemical group covalently bonded thereon, the chemical group being selected from the group consisting of:

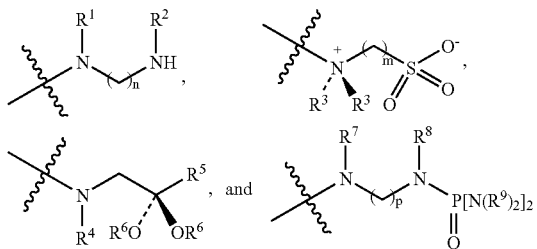

wherein $R^1$, $R^4$ and $R^7$ are the same or different and each is selected from the group consisting of hydrogen and a $C_1$-$C_6$ alkyl; $R^3$, $R^5$, $R^7$, $R^8$ and $R^9$ are the same or different and each is a $C_1$-$C_6$ alkyl. $R^6$ is a $C_1$-$C_6$ alkyl. m, n and p are the same or different and each is an integer greater than 0.

Another aspect of the present invention provides an article, comprising a substrate having covalently bonded thereon a polyamine via a linkage comprising the structure:

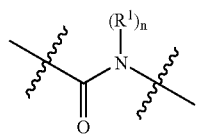

wherein $R^1$ is selected from the group consisting of hydrogen, a $C_1$-$C_6$ alkyl and an aryl, and n is an integer equal to 0 or 1, the article being resistant to the adsorption of proteins, cells or bacteria.

Another aspect of the present invention provides an article comprising a substrate covalently bonded to a substantially linear polymer comprising an amine in a repeat unit.

Another aspect of the present invention provides an article comprising a substrate covalently bonded to a polyamine via a linker selected from the group consisting of an amide, an amine, an ester, an ether, urea, a carbonate and an imine.

Other aspects of the invention feature an article capable of specific binding to a biomolecule while preventing undesired non-specific binding.

Thus, another aspect of the present invention provides an article comprising a substrate having a polymer bonded thereon. A surface of the polymer comprises a first region which is resistant to the adsorption of biomolecules. The surface of the polymer further comprises a second region comprising at least one chemical chain terminated with a group capable of being derivatized with a ligand for covalent bonding to an analyte.

Another aspect of the present invention provides an article comprising a substrate having covalently bonded thereon a polyamine, the polyamine being terminated with an oligo (ethylene glycol), group, wherein n is no more than 10, or any of the compositions claimed or listed herein, and mixtures of two or more of any of these compositions.

Other advantages, novel features, and objects of the invention will become apparent from the following detailed description of the invention when considered in conjunction with the accompanying drawings, which are schematic and which are not intended to be drawn to scale. In the figures, each identical or nearly identical component that is illustrated in various figures is represented by a single numeral. For purposes of clarity, not every component is labeled in every figure, nor is every component of each embodiment of the invention shown where illustration is not necessary to allow those of ordinary skill in the art to understand the invention.

BRIEF DESCRIPTION OF THE DRAWINGS

FIG. 1A shows a schematic of a gold surface covalently bonded to long chain alkane thiolates terminated with a carboxylic acid which are reacted to form an anhydride;

FIG. 1B shows a method for providing a chemical chain terminated with an amide;

FIG. 1C shows a schematic for covalently binding a polymer to a gold substrate surface;

DETAILED DESCRIPTION

Figure 2:
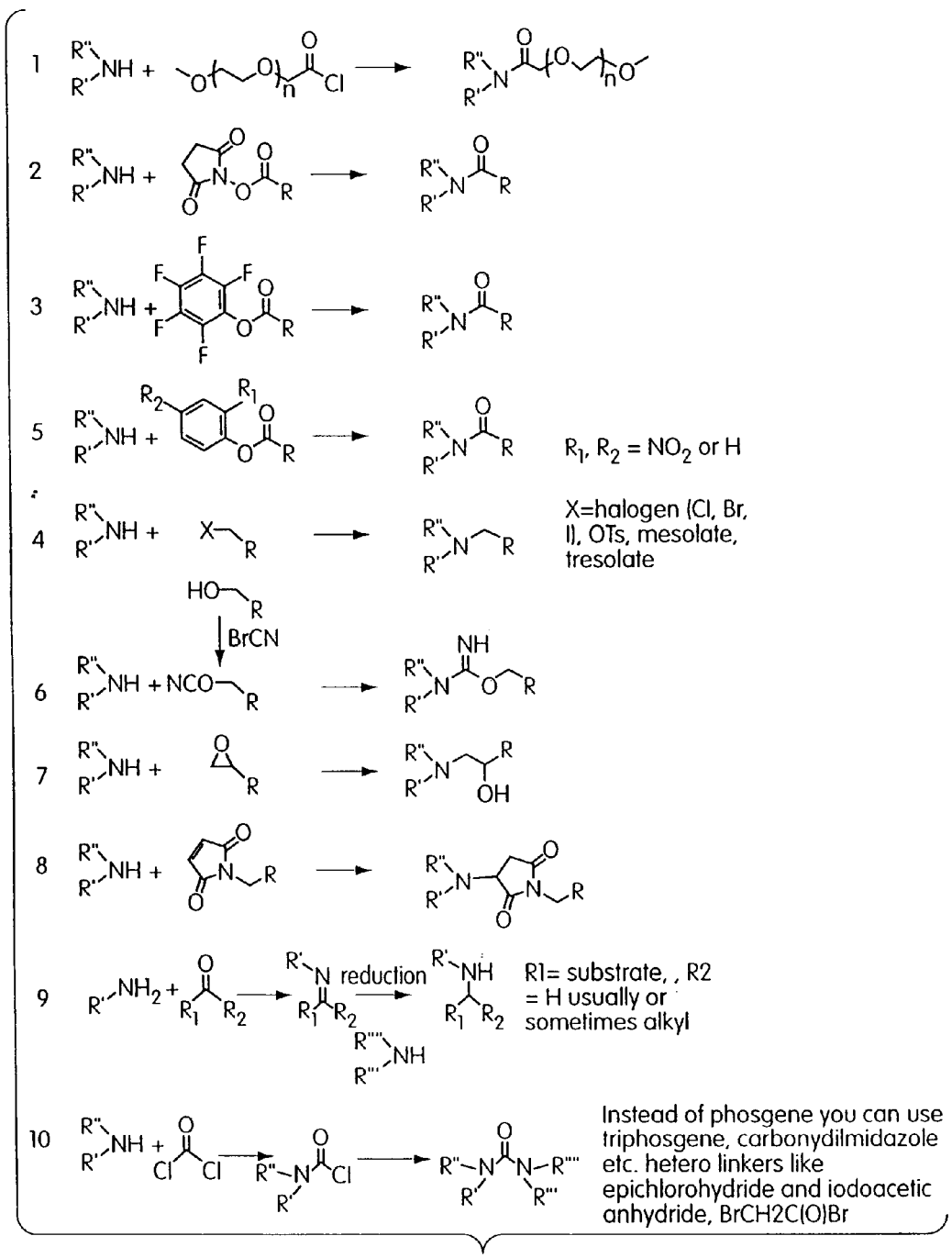
FIG. 2 shows a number of reactions that can be undertaken with a polyamine.

Much of current technology for preparing protein-resistant surfaces focuses on providing a low density coverage of high molecular weight (i.e. n>10) ethylene glycol oligomers or polymers. Alternative compositions are desired due to the susceptibility of oligo(ethylene glycol) (oligo-EG) or poly (ethylene glycol) (PEG) to autoxidation. The present invention relates to substrate surfaces derivatized with a variety of alternate compositions, resulting in several materials that show resistance to the adsorption and deposition of proteins, cells, and bacteria. Preparation of these materials is relatively facile, and thus the present invention provides surfaces that can be tailored for a particular application, whether it be anti-fouling of watercraft or other surfaces exposed to large quantities of moisture, materials for drug delivery (e.g. liposomes as drug delivery devices can be improved by grafting desired terminal groups to a lipid membrane), membranes, tissue substitutes, or wound dressings. Other applications include prevention of a wide variety of problems including: i) thrombosis caused by the adsorption of plasma proteins on in dwelling medical devices such as intravenous catheters; ii) irritation caused by the adsorption of proteins and the adhesion of bacteria to external medical devices such as contact lenses; iii) contamination of packaged food by microorganisms such as *Salmonella typhimurium* and *Staphylococcus aureus* that can lead to biofilm formation; and iv) "hard fouling": the adherence of barnacles and gorgonians to the hulls of ships. Protein and bacterial resistant surfaces are also for applications in biomedical devices and laboratory equipment.

In addition, the invention provides surfaces that specifically bind desired biomolecules, cells and bacteria.

One aspect of the present invention provides a substrate having covalently bonded thereon a chemical chain. The chemical chain can be covalently bonded to an outer surface of the substrate. Covalent bonding provides a more robust and stable article compared to surfaces that provide mere adsorption of chemical groups.

A chemical chain contains a single continuous bond pathway linking at least five atoms within the pathway. The chain is a linear chain although the chain can be bonded to other pendant chemical groups. Typically, the pendant chemical groups have smaller bond pathways than the main chemical chain. The chemical chain also comprises a biologically resistant group, i.e. the group capable of preventing adsorption of proteins, cells and/or bacteria. In one embodiment, the biologically resistant group is a terminal group. Typically, one end of the chain is covalently bonded to the substrate, and the terminal group is positioned on the other end of the chain. Thus, the terminal group terminates the longest continuous bond pathway initiating from the atom covalently bound to the substrate surface. However, the chain can be of sufficient length such that the chain has several bends, resulting in the terminus being buried under neighboring chemical chains. In this embodiment, the biologically resistant group is not necessarily a termina group, but rather the group that is "exposed". In this situation, the "terminal group" is not the actual terminus but rather a pendant group that is exposed and capable of preventing adsorption of proteins, cells or bacteria.

In one embodiment, the terminal group comprises the structure:

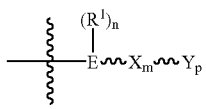

E is a heteroatom and can include nitrogen, oxygen, phosphorus or sulfur. X is an organic substituent and m is an integer less than or equal to 3; thus X may or may not be present, or a series of "X" groups may be linked sequentially. $R^1$ can be hydrogen, a $C_1$-$C_6$ alkyl and an aryl, and n is an integer less than or equal to 2. Y is an organic group and can include amides, amide derivatives, amines, amine derivatives, cyclic ethers, sugar derivatives, amino acids, amino acid derivatives, or multiple nitrites; p is an integer greater than 0. ⋎⋏⋎⋏⋎represents one or more single bonds, a double bond, or any combination thereof. Optionally $R^1$ can bond to X or Y to form a cyclic structure. One or more atoms can be used to link $R^1$ to X or Y. Thus, E can be part of a ring structure, such as a heterocycle.

X and Y are free of a hydrogen-bond donor. A hydrogen-bond donor has a hydrogen covalently attached to a heteroatom (non-carbon atom) that is capable of interacting with a lone electron pair. The terminal group is also hydrophilic, i.e., the terminal group has an affinity for water (adsorbs, binds, or otherwise fails to repel water). Hydrophobic groups typically cause protein adsorption.

Without wishing to be bound by any theory, it has been suggested that protein adsorption is related to the ability of a protein to displace water from a surface. A hydrophilic surface tends to retain the water and prevent displacement of water by the protein. Hydrogen-bond donors present in X or Y groups can potentially interact with large numbers of hydrogen-bond acceptors in proteins, thus reducing the protein-resistant properties. However, if a hydrogen-bond donor group is buried beneath other substituents of the chain, e.g., the chain has sufficient steric bulk, then the hydrogen-bond donor group will most likely affect protein-resistant properties very minimally. Thus, in one embodiment, the article of the invention exposes a surface free of hydrogen-bond donor groups. "Exposes" refers to regions of the surface capable of preventing the adsorption of proteins, cells or bacteria.

Preferably, the chemical chain, or at least a portion of the chain such as the terminal group or the exposed group, has properties that render the article resistant to the adsorption of proteins, cells, or bacteria. In one embodiment, resistance to the adsorption of proteins is determined by measuring the percentage of a monolayer that adsorbs onto a surface under a given set of conditions. The extent of protein adsorption can be determined with the use of a Biacore 1000 SPR. Surface plasmon resonance (SPR) provides a label-free analytical method to measure the adsorption and/or desorption of biomolecules to surfaces. A protein solution in buffer is provided in a concentration of 1 mg/mL and is flowed at a rate of 10 μL/min over the substrate surface for 30 min. A solution of buffer is flowed over the surface for 10 min prior to taking a reading. A fully hydrophobic surface is used as a control; typically a surface containing a monolayer of a chain of alkyl groups. This surface would adsorb 100% of a monolayer. The amount of protein adsorbed (ΔRU=change in response units) as measured by SPR can be determined by subtracting the value of RU (RU=reflectance units measured by SPR) prior to the injection of protein from the value of RU measured 10 min after the completion of a 30 min protein injection. The value of ΔRU is then used to calculate the percentage of a monolayer (% Monolayer) of that protein relative to a fully hydrophobic surface using eq 1.

$$\% \ ML = \% \ \text{Monolayer} = \frac{\Delta RU_{test \ surface}}{\Delta RU_{hydrophobic \ surface}} \times 100 \quad (1)$$

Thus, compositions of the present invention can be screened by choosing terminal groups having properties as mentioned above and monitoring the extent of protein adsorption in relation to a fully hydrophobic surface. In one embodiment, the article is resistant to the adsorption of proteins such that the article adsorbs no more than 60% of a monolayer of proteins, as compared to a hydrophobic surface (100%) under the same conditions. Preferably the article adsorbs no more than 50% of a monolayer of proteins, more preferably no more than 40% of a monolayer, more preferably no more than 30% of a monolayer of proteins, more preferably no more than 20%, more preferably still no more than 10%, and even more preferably no more than 5%.

Without wishing to be bound by any theory, characteristics for protein-resistance bear some correlation to those for bacterial-resistance and cell-resistance. The correlation is not necessarily linear, however (see Example 2).

The adhesion of bacteria can be determined by measuring a number of bacterial colonies that are attached to surfaces (colony forming units, cfu/mL). Colonies are removed from the surfaces via sonication and subsequently grown in appropriate media for a fixed amount of time. Colony counts are measured by determining their optical density. Sonication is not always an efficient method for removing adhered bacteria, especially in the case of control gold surfaces. Thus, control values reported herein may be somewhat low.

In particular, two bacterial strains, *Staphylococcus epidermidis* and *Staphylococcus aureus*, are known to cause 30-50% of infections on in-dwelling devices, i.e., a device implanted in the human body, such as a catheter or a heart defibrillator. *E coli* strains are found in patients suffering from urinary tract infections. Without wishing to be bound by any theory, bacterial adsorption (or infection) occurs via the adsorption of proteins (presented by the host or secreted by the pathogen) to the surface of the device. Bacteria can adhere to and grow on this surface. Formation of a carbohydrate gel layer covering the bacteria often hides them from the immune system. In all cases, it appears that the presence of a layer of protein on a surface facilitates (or is required for) the adhesion of bacteria. Surfaces that resist the adsorption of proteins are, therefore, strong candidates as surfaces that resist the adhesion of bacteria.

Without wishing to be bound by any theory, mammalian cells generally attach to a layer of protein adsorbed on a surface. In addition, mammalian cells can secrete their own matrix onto a surface that promotes the adsorption of proteins, in a process known as "remodelling."

In one embodiment, the terminal or exposed group includes a hydrogen-bond acceptor group. Hydrogen-bond acceptor groups include an atom having an available pair of electrons to interact with a proton from a hydrogen-bond donor. Hydrogen-bond acceptor groups include atoms such as oxygen, nitrogen, phosphorous, and sulfur. In one embodiment, the hydrogen-bond acceptor group is the "E" group, although the hydrogen-bond acceptor can also be positioned within the X or Y groups of the terminal group.

In one embodiment, the terminal group has an overall neutral charge. An overall neutral charge is provided by a terminal group lacking any charged atoms or groups. Alternatively, one atom or group can be charged but the terminal group would also include charged species of an equal and opposite charge to neutralize the terminal group. An example of this arrangement is a zwitterion, such as in an amino acid. A terminal group having an overall neutral charge is distinguished from a terminal group which is neutralized by an external counterion in which the counterion is not covalently bonded to any portion of the chemical chain. In one embodiment, the entire chemical chain has an overall neutral charge.

In another embodiment, a terminal group of a chain is charged and is neutralized by at least one neighboring terminal group of an opposite charge. For example, a terminal group having a +1 charge can be neutralized by an adjacent terminal group having a −1 charge. Alternatively, if a terminal group has a higher charge, it can be neutralized by one terminal group of an equal and opposite charge or by two or more terminal groups having sufficient charge for neutralization.

In one embodiment, the substrate has covalently bonded thereon a plurality of chemical chains free of cross-linking. Chains free of cross-linking provide a longer effective chain length, providing the chain with more mobility to orient and arrange water molecules. This capability may affect the ability to resist adsorption of proteins. Alternatively, there may be a small amount of cross-linking, preferably between atoms close to the substrate surface, but this arrangement still provides a chain of sufficient length. In another embodiment, the article comprises a monolayer of a plurality of chemical chains bonded to the surface. A monolayer comprises a plurality chemical chains covalently bonded to the surface which are sufficiently free of other chemical species adsorbed thereon. In one embodiment, the monolayer is a self-assembled monolayer. Self-assembled monolayers (SAMs) involve chemical chains having a functional group which selectively attaches to the substrate surface such that the remainder of the chain interacts with neighboring chains in the monolayer to form an ordered array. SAMs have been formed on a variety of substrates including metals such as silver or gold, and ceramics such as silicon dioxide or gallium. Other materials and methods for the formation of SAMs are described in U.S. Pat. No. 5,512,131, entitled "Formation of Microstamped Patterns on Surfaces and Derivative Articles" by Kumar et al., filed Oct. 4, 1993, and PCT Publication No. WO 96/29629, entitled "Microcontact Printing on Surfaces and Derivative Articles" by Whitesides et al., published Jun. 26, 1996, each of which is incorporated herein by reference.

The plurality of chemical chains can be homogenous, i.e., all the same composition, or include two or more different compositions. In one embodiment, the chemical chain is a first chemical chain and the monolayer further comprises a second chemical chain having a different composition from the first chemical chain. The second chemical chain is present in the monolayer in an amount of less than about 75% of the total of the first and second chemical chains. This mixture of different compositions is also referred to as a "mixed SAM." Mixed SAMs allow the surface to be tailored for a particular application. For example, some mixed SAMs show resistance to protein adsorption when present in an amount as low as 25% of the total of chemical chains. For example, it may be advantageous to minimize the amount of first chemical chain from the monolayer if the first chemical chain is particularly difficult and/or expensive to prepare. Mixed SAMs may also be advantageous when one chain is bulky in size or does not form ordered arrays as a single component SAM. Or, the percentage of first chemical chain in the monolayer can be fine-tuned depending on the amount of adsorption desired. For certain applications, the second chemical chain is present in an amount of less than about 50% of the total of chemical chains and in other applications, the second chemical chain is present in an amount of less than about 25% of the total of chemical chains. Of course, three or more different SAM types can be readily contemplated.

It is not necessary that the second chemical chain has properties that render the article resistant to the adsorption of proteins so long as the first chain has protein-resistant properties, and the properties of the first chain dominate the properties of the overall article. For example, the first chain may be of sufficient length or bulk to cover the second chain which lacks protein-resistant properties, e.g. the second chain no longer has an "exposed" terminal group as it is blocked by the first chain. In one embodiment, the second chemical chain has a terminal group including a $C_1$-$C_{25}$ alkyl, and aryl, a carboxylic acid, a thiol, a hydroxyl and a quaternary ammonium ion. In another embodiment, the second chemical chain has properties that allow the article to be capable of resisting the adsorption of proteins. In this embodiment, the second chemical chain can have a terminal group comprising a similar structure as that for the first chemical chain.

In one embodiment, the second chemical chain has a smaller average length than an average length of the first chemical chain. As described previously, chain length is determined by measuring the distance of the continuous bond pathway linking the atom of the chain bonded to the substrate and the terminal group. This arrangement is advantageous, for example, in the situation where the second chemical chain lacks protein resistant properties yet is present in the monolayer to cover all surfaces of the substrate and/or provide high density coverage. The taller first chemical chain has fully exposed terminal groups to exploit the protein resistant properties of the terminal groups. If the first chemical chain is sufficiently longer than the second chain, preferably by at least 5, 10, or 15 atoms, the first chain can effectively shield the second chain.

In one embodiment, the chemical chain is the terminal group. This embodiment can apply to shorter chemical chains in which all the atoms of the chemical chain contribute to the protein resistant properties of the article.

Substrates can be of any material capable of forming a covalent bond to any of the compositions listed herein. Typical substrates comprise metals, alloys, ceramics or plastics. Surfaces of interest include silica, alumina, quartz, glass, and the like or derivatives thereof, or metals such as gold, silver and copper. Plastics of interest include polyethylene, polypropylene, polystyrene, polycarbonates, polyurethane, and polydimethylsiloxane. Protein-resistant coatings can be applied to articles and devices such as those used in the manufacture of in-dwelling devices (i.e., devices implanted in humans) such as catheters, heart defibrillators, or any artificial bone or joint replacements. Any material used to make these articles and devices can also function as the substrate.

In one embodiment, the chemical chain comprises a terminal group and a linker covalently bonded to the terminal group and to the substrate. A linker is derived from a molecule having two functional groups capable of covalent bonding to another species. Typically, the two functional groups are positioned at either extreme of the linker. For example, the linker can comprise a chain of atoms in which one end of the chain has a functional group capable of bonding to the substrate and the other end of the chain has a functional group capable of bonding to the terminal group. The linker can be as small as a single atom, i.e., an oxygen or sulfur atom or as large as a polymer. The linker can comprise a chain of two or more atoms such as an amide linker.

Other examples of linkers comprise the following structure:

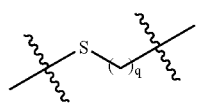

wherein q is an integer greater than 0;

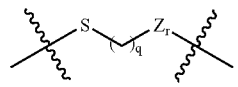

wherein Z comprises a heteroatom, and r is equal to 0 or 1; and

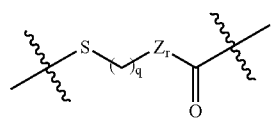

Z is a heteroatom capable of forming two single covalent bonds, such as oxygen, nitrogen, silicon or sulfur.

refers to a covalent bond to another species.

In one embodiment, the chemical chain comprising a terminal group and a linker comprises the structure:

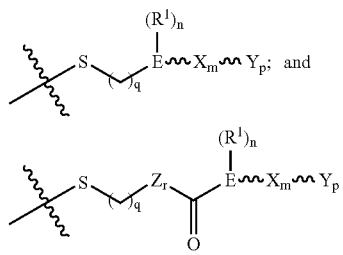

To provide an increased chain length, q can be an integer greater than 3.

In one embodiment, the substrate comprises a first composition and a chemical chain comprises a second composition different from the first composition. For example, the chemical chain is typically a molecular or polymeric species and the substrate comprises a material such as a metal, a ceramic, and a polymer. Examples of metals include gold and silver. Examples of ceramics include silica.

In one embodiment, the terminal group comprises the structure:

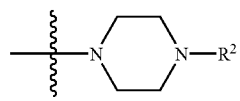

wherein $R^2$ can be a $C_1$-$C_6$ alkyl, an ether, an ether derivative, an ester, a formyl, a carboxyl, or $C(O)R^3$ in which $R^3$ is a $C_1$-$C_6$ alkyl. This terminal group is a piperazine unit in which Y comprises a variety of amines or amine derivatives.

In one embodiment, Y is an amide. Y can be an amide comprising the structure:

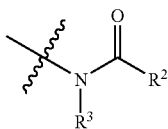

wherein $R^2$ and $R^3$ are the same or different and each is a $C_1$-$C_6$ alkyl. Other examples of terminal groups having Y as an amide include a terminal group comprising the structure:

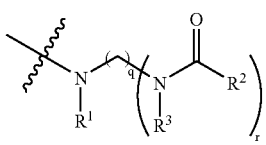

wherein $R^2$ comprises a terminal or linking $C_1$-$C_6$ alkyl, and each of q and r is an integer greater than 0. In this structure, the amide bound by parentheses ( ) can comprise several amides linked together and terminating in an amide. Thus, the terminal amide has a $R^2$ comprising a terminal $C_1$-$C_6$ alkyl whereas inner amides have an $R^2$ comprising a linking $C_1$-$C_6$ alkyl.

In one embodiment, Y is an amide comprising the structure:

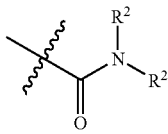

Example terminal groups incorporated in this type of amide include the structure:

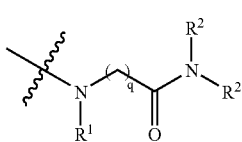

wherein q n is an integer greater than 0; and

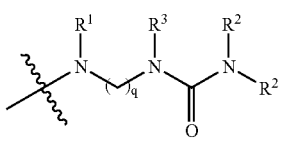

wherein $R^3$ is a $C_1$-$C_3$ alkyl and q is an greater than 0.

The terminal group can include amino acids or amino acid derivatives. In one embodiment, Y comprises the structure:

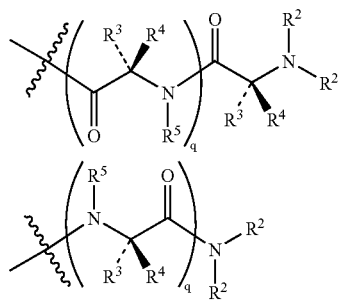

wherein the group enclosed within parenthesis represents an amino acid or an amino acid derivative, $R^2$ is a $C_1$-$C_6$ alkyl, and $R^3$, $R^4$ and $R^5$ can be the same or different and each can be an organic group. q is an integer greater than one.

In one embodiment, $R^2$ is a methyl or ethyl group. Any amino acid can be used in accordance with the present invention. One example of an amino acid is glycine. An amino acid can be functionalized, for example, at the N-terminus. N-methyl glycine is an example of an N-alkylated ($C_1$-$C_6$ alkyl) amino acid.

In one embodiment, Y is an amine. An example amine comprises the structure:

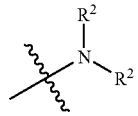

wherein $R^2$ is a $C_1$-$C_6$ alkyl.

In one embodiment, the terminal group is a cyclic ether. Examples of cyclic ethers include:

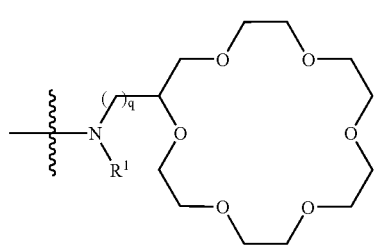

wherein $R^1$ is a $C_1$-$C_6$ alkyl, q is an integer greater than or equal to 0; and

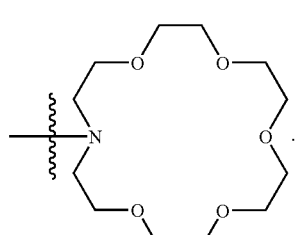

Of course, larger or smaller ring ethers are also within the scope of the invention.

In one embodiment, Y comprises a sugar derivative. Example sugar derivatives involve a sugar peralkylated with a $C_1$-$C_6$ alkyl. In one embodiment, the terminal group comprises the structure:

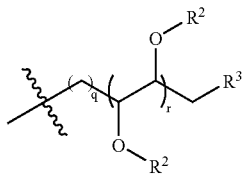

wherein $R^2$ and $R^3$ are the same or different and each is a $C_1$-$C_6$ alkyl, q and r are the same or different and each is an integer greater than 0.

In one embodiment, Y comprises a multiple nitrile group, i.e., more than one nitrile. In one embodiment, Y comprises a structure:

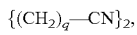

wherein q is greater than 0. In another embodiment, the terminal group comprises a structure:

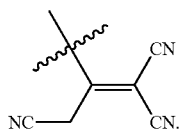

Specific examples of the biologically resistant groups of the invention are listed in Table 1. In some embodiments, the invention encompasses surfaces covalently bonded to biologically resistant groups of Table 1 which adsorbs no more than 60% of a monolayer of proteins as compared to a hydrophobic surface, as described previously, and preferably no more than 50%, 40%, 30%, 20%, 10% and more preferably no more than 10% of a monolayer of proteins. In other embodiments, selections of two or more species listed in Table 1 having the previously described protein adsorption characteristics are encompassed within the present invention.

Another aspect of the present invention provides an article comprising a substrate having covalently bonded thereon a monolayer of chemical chains. At least 25% of the chains of the monolayer are terminated with a hydrophilic group free of a hydrogen-bond donor. In other embodiments, at least 50% of the chains are terminated with the hydrophilic group and in other embodiments, at least 75% of the chains of the monolayer are terminated with the hydrophilic group. In other embodiments, all the chains are terminated the hydrophilic group. The hydrophilic group includes amides, amide derivatives, amines, amine derivatives, cyclic ethers, sugar derivatives, amino acids, amino acid derivatives, and multiple nitriles. The article is resistant to the adsorption of proteins, cells, or bacteria.

The monolayer can have any or all of the features previously described. The monolayer can be a self-assembled monolayer. The hydrophilic group can include a hydrogen-bond acceptor group. Each chemical chain of the monolayer has an overall neutral charge. Alternatively, if a chemical chain of the monolayer is charged, it is neutralized by at least one neighboring chemical chain of an opposite charge.

The monolayer can include a linker group to bond the hydrophilic group to the substrate. In one embodiment, the linker group has a substantially straight-chain backbone, i.e., the linker group has a minimal number of pendant groups. In one embodiment, the linker backbone comprises at least three atoms. This rigid backbone can comprise a straight chain of methylene groups and preferably at least three methylene groups. Optionally, the chain of methylene groups can be interrupted by at least one heteroatom such as nitrogen, oxygen, phosphorous or sulfur. Alternatively, the straight chain of methylene groups can be interrupted by an amide, a ketone, an ester, or an ether group.

The present invention features other chemical groups that are effective for resisting the adsorption of proteins bonding to a substrate. Thus, another aspect of the present invention provides an article comprising a substrate having a chemical group covalently bonded thereon. Examples of these chemical groups include:

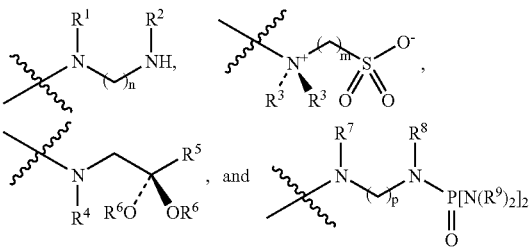

wherein $R^1$, $R^4$ and $R^7$ are the same or different and each is selected from the group consisting of hydrogen and a $C_1$-$C_6$ alkyl; $R^3$, $R^5$, $R^7$, $R^8$ and $R^9$ are the same or different and each is a $C_1$-$C_6$ alkyl; $R^6$ is a $C_1$-$C_6$ alkyl; and m, n and p are the same or different and each is an integer greater than 0. The article is resistant to the adsorption of proteins, cells or bacteria. In one embodiment, each of $R^1$-$R^4$, $R^6$, $R^7$, $R^8$ and $R^9$ is a methyl group.

Another aspect of the present invention provides articles resistant to the adsorption of proteins, cells or bacteria in which a substrate has covalently bonded thereon a polymer, such as a polyamine. A polymer layer on a substrate surface could potentially provide homogenous coverage and cover-up any pinhole heterogeneities which may be present in the underlying substrate. Polymers would also provide a robust surface for materials to be used as biomedical devices. Depending on the polymer composition, a polymer layer could have gel-like character which is a physical property that can contribute to the resistance of protein adsorption. Ideally, the polymer can be functionalized with a variety of different groups to generate inert surfaces. Finally, polymers can provide a high density of groups that can be functionalized to render the surface resistant to the adsorption of proteins.

Poly(ethylene glycol) (PEG) has been used extensively as a component in materials for biomedical applications, particularly in biomedical devices to decrease the adsorption of proteins. However, PEG has a tendency to autoxidize when exposed to $O_2$ and transition metals. In vivo, the terminal hydroxyl group of PEG is oxidized to aldehyde by alcohol dehydrogenase; the aldehyde group is oxidized further by aldehyde dehydrogenase.

Although polyamines such as poly(ethylenimine) (PEI) are known to resist the adsorption of proteins, this aspect of the present invention features robust linkages to bond the polyamine covalently to the substrate. In one embodiment, the linkage comprises the structure:

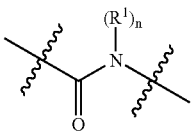

wherein $R^1$ is selected from the group consisting of hydrogen, a $C_1$-$C_6$ alkyl and an aryl, and n is an integer equal to 0 or 1, the article being resistant to the adsorption of proteins, cells or bacteria. The polyamine can be bonded via the nitrogen to form an amide bond. In one embodiment, the linkage comprises the structure:

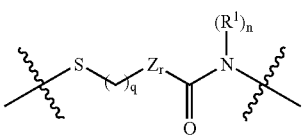

wherein p is an integer greater than 1, Z comprises a carbon atom or a heteroatom, and r is equal to 0 or 1. In one embodiment, q is less than 10. Z can be a heteroatom such as oxygen, nitrogen, phosphorous, or sulfur.

Polyamines can have hydrogen-bond donor groups that can interfere with protein-resistant properties. In one embodiment, the polyamine is derivatized to be free of a hydrogen-bond donor group. In one embodiment, the derivatization involves acylating the polyamine. Acylation allows the polyamine to be derivatized with a variety of functional groups that are known for conveying protein-resistant characteristics, and thus an acylating agent is a convenient method for conveying these functional groups to a polymeric surface. This method of providing protein-resistant functional groups is particularly advantageous because polyamines contain a large number and high density of acylation sites, and thus acylation provides a high density of functional groups to provide a surface resistant to the adsorption of proteins.

In addition, polyamines are particularly advantageous in that exposed amino groups are excellent nucleophiles that can react efficiently with other electrophiles such as carboxylic anhydride groups. This reactivity can provide a mechanism for attaching a polyamine onto a surface (see FIG. 1 and accompanying discussion below).

Certain prior art materials provide a cross-linked polymer as a protein-resistant surface. Many cross-linking groups, however, are hydrophobic and this hydrophobicity can decrease the capability of the article to resist the adsorption of proteins. In one embodiment, the polyamine of the present invention is free of cross-linking. Cross-linking is known to improve the stability of the polymer. The present invention provides stable covalent linkages such that extensive cross-linking is unnecessary.

"Polyamine" refers to any molecule having at least two repeat units, in which each repeat unit includes an amino group. Preferably, the polyamine has at least four repeat units, more preferably at least six repeat units, even more preferably at least eight repeat units, and even more preferably still, at least 10 repeat units.

Figure 4:
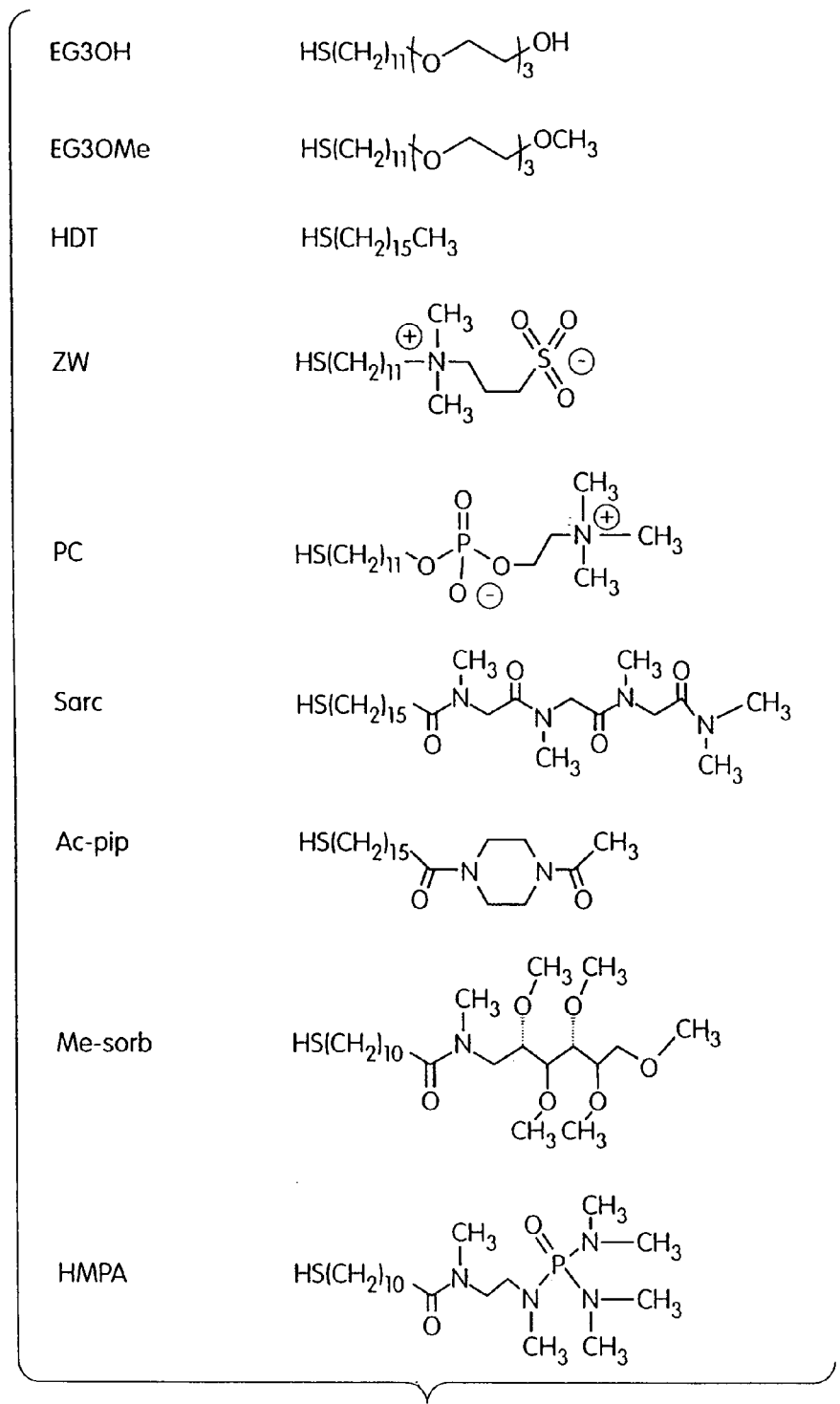
FIG. 4 shows structures of chemical chains, as described in Example 2.

Examples of polyamines include linear poly(ethylenimine) (LPEI), branched poly(ethylenimine) (BPEI), poly (N-methyl-vinylamine) (PMVA), poly(allylamine) (PAA) and poly(L-lysine) (PLYS) see (FIG. 4).

LPEI, PMVA, PAA and PLYS are linear polymers free of branching or cross-linking. BPEI is a highly cross-linked polymer. For example, BPEI can comprise a 1:2:1 ratio of primary:secondary:tertiary amino groups. BPEI can have significantly more primary amino groups than LPEI and upon acylation, these amino groups retain a hydrogen-bond donor group (HNCOR). Without wishing to be bound by any theory, a highly cross-linked film of BPEI can provide steric repulsion to prevent adsorption of the protein, and such steric repulsion may counterbalance any unfavorable contributions to the adsorption energy of the large number of hydrogen-bond donor groups in the BPEI film.

This aspect of the invention also provides other linkers to bond a polyamine to a substrate in a stable, covalent fashion. Such linkers, which are not part of the original polymer, include an ester, an ether, an amine, an amide, urea, a carbonate, and an imine. The polyamine can be any of the polyamines previously mentioned.

The substrate surface can comprise a homogenous distribution of polyamines having the same composition. Mixtures of polyamines with other polyamines or other chemical species can be envisioned. In one embodiment, the polyamine comprises a first chemical chain and a substrate further has covalently bonded thereon a second chemical chain in an amount of less than 75% total of the chemical chain. The second chemical chain can comprise a polyamine as listed previously. Alternatively, the second chemical chain can comprise any chemical chain having a terminal group as described previously. In one embodiment, the second chemical chain can be present in an amount of less than 50% total of the chemical chain. In other embodiments, the second chemical chain can be present in an amount of less than 25% total of the chemical chain.

Another aspect of the present invention provides an article comprising a substrate covalently bonded to a substantially linear polymer comprising an amine and a repeat unit. The article is resistant to the adsorption of proteins, cells or bacteria. Substantially linear polymers comprise long chain pathways, and preferably the linear polymer is free of cross-linking. Examples of linear polymers include linear poly(ethylenimine), poly(N-methyl-vinylamine), poly(allylamine) and poly(L-lysine).

The chemical chains, terminal groups or polymers can be covalently bonded to a substrate by a number of methods. One example is schematically shown in FIG. 1. FIG. 1A shows a gold surface covalently bonded to a long chain alkanethiolate terminated with a carboxylic acid, and methods for providing such surfaces are well known in the art. Neighboring carboxylic acids can be reacted with each other to form an anhydride. FIG. 1B shows a method for providing a chemical chain terminated with an amide. In FIG. 1B, reaction of the anhydride with a primary amine produces alkanethiolate chains terminated with secondary amides. Thus, the alkanethiolate serves as a linker group. Of course, other reactions can be carried out other than that showed in FIG. 1 to add other terminal groups of the invention.

Another aspect of the present invention provides a surface having covalently bonded thereon a polyamine in which the polyamine is terminated by a oligomers such as oligo (ethylene glycol). These oligomers can have a chain of no more than 10 ethylene glycol groups, preferably no more than eight, more preferably no more than six, more preferably no more than four, and even more preferably two ethylene glycol groups.

FIG. 1C shows an example of a method for covalently binding a polymer to a gold substrate surface. FIG. 1C shows a reaction of linear polyethylenimine (LPEI) directly with the anhydrides. After acylation, LPEI is free of hydrogen-bond donor groups to provide a protein-resistant surface, or at least the portion of LPEI that was exposed to a solution of acylating agent.

FIG. 2 shows a number of reactions that can be undertaken with a polyamine. In equations 1-8 and 10 of FIG. 2, the polyamine is schematically shown as H—N(R')(R"). R' of equations 1-10 can represent a substrate surface. R" can represent another chemical group or the remainder of the polymer. Reaction 1 of FIG. 2 shows a method for binding an oligo(ethylene glycol), group (n=10 or less) to an amine group of polyamine. Equations 2, 3 and 5 show other methods for adding an acyl group to the polyamine, in which the acyl group has various "R" functionalities. Equations 4 and 6-10 show methods for derivatizing the polyamine with a variety of other chemical groups that can enhance protein resistant properties. Conversely, "R" of FIG. 2 can be the substrate surface and equations 2-8 show methods for linking a polyamine to a substrate surface. In equation 10, R'" can represent a substrate surface.

Another aspect of the present invention provides a surface capable of biospecifically binding to a biomolecule. Certain prior art surfaces involve covalent attachment of a ligand that is specific for a biomolecule. The ligand, however, typically is present in only discrete areas of the surface whereas other regions of the surface remain exposed. Thus, these prior art surfaces suffer in that these exposed regions are capable of binding with the desired biomolecule and do not prevent non-specific binding of any other biomolecule.

The present invention is particularly advantageous over certain prior art surfaces in that it provides an inert surface to prevent undesired non-specific binding by providing discrete regions which are derivatized with groups capable of specifically binding a biomolecule via covalent attachment. This aspect of the invention provides an article comprising a substrate having a polymer bonded thereon to provide a polymer surface on the substrate. The surface of the polymer in turn comprises a first region resistant to the adsorption of biomolecules. A second region of the polymer surface, generally contiguous with the first region, comprises at least one chemical chain terminated with a group capable of being derivatized with a ligand specific for a biomolecule or any analyte. The resulting article is capable of biospecific binding to a biomolecule and prevents non-specific binding of any biomolecule. Thus, upon approach of the biomolecule to the surface of the present invention, if the biomolecule contacts the first region, it will not adsorb. If the biomolecule contacts the ligand site in the second region, it will bind to it biospecifically. The bound biomolecule can also be used to further bind a second biomolecule from solution; an example of this includes biospecific binding of a first antibody to a surface, followed by biospecific binding of a second antibody via the first antibody.

The biomolecule can range in size from a small molecule such as a benzene sulfonamide group to a large molecule such as a protein. Other examples of biomolecules include antibodies, DNA, RNA, nucleotides, nucleosides, carbohydrates, peptides. Cells and bacteria can also bind to such surfaces biospecifically.

The first region can comprise the polymer itself, in which the polymer is resistant to the adsorption of proteins, cells and bacteria. The polymer can be any polymer as described herein. In one embodiment, the polymer surface can have a plurality of chemical chains bonded thereon, or another polymer bonded thereon, in which the chemical chains or polymer is resistant to the adsorption of proteins, cells and bacteria. The chemical chains can comprise any terminal group as described previously or an oligo(ethylene glycol) having a chain length of no more than 10 ethylene glycol groups, preferably no more than 8, 6, 4 and even more preferably two ethylene glycol groups. In addition, the chemical chains can comprise any mixture of two or more terminal groups or oligo(ethylene glycol) groups of the above-recited chain lengths, as described herein.

"A chemical chain terminated with a group capable of being derivatized with a ligand" refers to any chain having a reactive terminal group. The reactive terminal group can undergo a reaction with a ligand precursor to provide a chain terminated with a ligand. The second region can comprise at least one chemical chain yet statistically the second region will comprise a single chain to maintain a low density of covalently bonded ligands.

Figure 15:
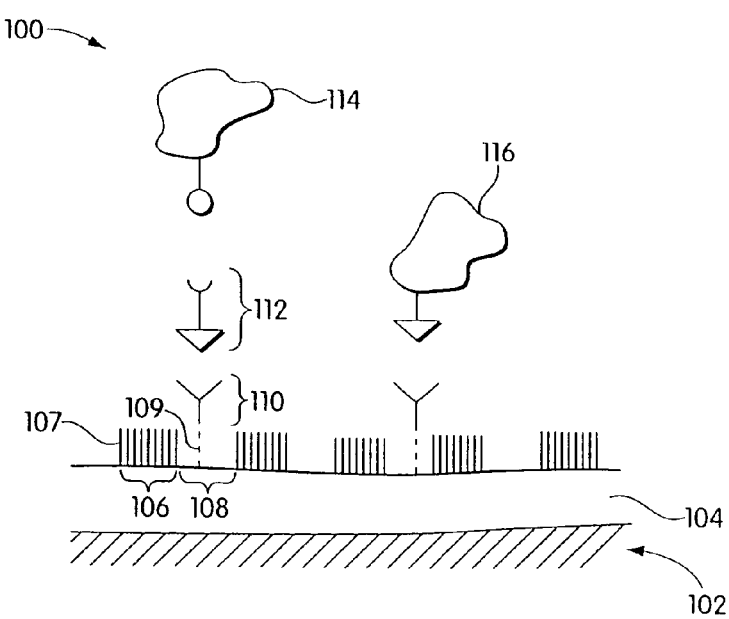
FIG. 15 shows a schematic example of an article capable of biospecific binding.

FIG. 15 shows a schematic example of an article of the present invention capable of biospecific binding. FIG. 15 shows article 100 comprising a substrate surface 102 having a polymer 104 bonded thereon. First region 106 comprises a plurality of chemical chains 107 covalently bonded to polymer 104. First region 106 is resistant to the adsorption of biomolecules. Second region 108 comprises at least one chemical chain 109 terminated with a ligand 110 capable of covalent binding to an analyte 112. Analyte 112 can be a biomolecule or any chemical species capable of binding to a biomolecule. Analyte 112, in turn, is capable of biospecific binding to biomolecule 114. Alternatively, ligand 110 itself is capable of binding a biomolecule, such as biomolecule 116. For example, ligand 110 can comprise a chemical species capable of binding a protein which is specific for a particular antibody. Other examples include covalent immobilization of avidin which has a high affinity for binding biotin or vice versa.

The function and advantage of these and other embodiments of the present invention will be more fully understood from the examples below. The following examples are intended to illustrate the benefits of the present invention, but do not exemplify the full scope of the invention.

EXAMPLE 1

SAMs That Resist the Adsorption of Proteins

Materials.

All chemicals used were reagent grade unless stated otherwise. Fibrinogen (from bovine plasma, F8630), lysozyme (egg white, E.C. 3.2.1.17, L6876), sodium dodecylsulfate (SDS), and phosphate buffered saline packets were purchased from Sigma (St. Louis, Mo.). Anhydrous N-methyl-2-pyrrolidinone (NMP), 16-mercaptohexadecanoic acid, trifluoroacetic anhydride (TFAA), N,N'-dimethyl-1,2-diaminoethane (HN(CH$_3$)CH$_2$CH$_2$N(CH$_3$)H), N,N,N'-trimethyl-1,2-diaminoethane (HN(CH$_3$)CH$_2$CH$_2$N (CH$_3$)$_2$), CH$_3$(CH$_2$)$_{11}$NH$_2$, 1-amino-1-deoxy-D-sorbitol, di-tert-butyl dicarbonate, diisopropylethylarnine (DIPEA), sodium hydride, methyl iodide, tetramethyl phosphorodiamidic chloride ((CH$_3$)$_2$N)$_2$P(O)Cl, and hydrazine were purchased from Aldrich (Milwaukee, Wis.). H$_2$NCH$_2$CON (CH$_3$)$_2$, (H$_2$NCH$_2$CONH$_2$) and HN(CH$_3$)CH$_2$CON(CH$_3$)$_2$ were purchased from BACHEM (Bubendorf, Switzerland). Tri(ethylene glycol)monoamine (H$_2$N(CH$_2$CH$_2$O)$_3$H) was a gift from Texaco Chemical Company, which has since been bought by Huntsman Corporation (3040 Post Oak Boulevard, Houston, Tex. 77056 (713-235-6000). Anhydrous N,N-dimethyl formamide (DMF), triethylamine, trifluoroacetic acid (TFA), acetic anhydride and ethylene glycol were purchased from EM Science (Gibbstown, N.J.). Absolute ethanol was purchased from Pharmco Products (Brookfield, Conn.). tert-Butyl N-methyl-N-[2-(methylamino)ethyl]carbonate ($HN(CH_3)CH_2CH_2N(CH_3)COC(CH_3)_3$) (Saari, W. S.; Schwering, J. E.; Lyle, P. A.; Smith, S. J.; Engelhardt, E. L. *J Med. Chem.* 1990, 33, 97-101) and N-carbomethoxy-N,N'-dimethyl-1,2-diaminoethane ($HN(CH_3)CH_2CH_2N(CH_3)CO_2CH_3$) (Cravey, M. J.; Kohn, H. *J. Am. Chem. Soc.* 1980, 102, 3928-3939) were synthesized as described previously. Phosphate-buffered saline (PBS: 10 mM phosphate, 138 mM NaCl, and 2.7 mM KCl) was freshly prepared in distilled, deionized water and filtered through 0.22 μM filters prior to use.

Preparation of the Reactive SAM Presenting Interchain Carboxylic Anhydride.

Gold substrates for SPR spectroscopy were prepared by e-beam evaporation of 1.5 nm of Ti, followed by 38 nm of Au, onto 50×18 mm² glass coverslips. The gold substrates were incubated, overnight, in a 2 mM solution of $HS(CH_2)_{15}CO_2H$ in ethanol/water/acetic acid (85/10/5, v/v/v), rinsed with ethanol, and dried under a stream of nitrogen. The cleaned substrates were then placed in a freshly prepared solution of 0.1 M trifluoroacetic anhydride (TFAA) and 0.2 M triethylamine in anhydrous DMF without stirring for 20 minutes at room temperature. The substrates were removed from the TFAA solution, rinsed thoroughly with $CH_2Cl_2$ and dried in a stream of nitrogen. The resulting substrates (which present interchain carboxylic anhydride groups) were used immediately by immersion into a 10 mM solution of the appropriate amine in NMP. We added triethylamine (20 mM in NMP) to the amino compounds purchased as salts. 1-Amino-1-deoxy-D-sorbitol was not soluble in NMP; this reaction was carried out in a 25 mM phosphate buffer, pH 10, 10 mM 1-amino-1-deoxy-D-sorbitol (see Table 1). The substrates were removed from the amine solution, rinsed with ethanol and dried under a stream of nitrogen.

Surface Plasmon Resonance Spectroscopy (SPR).

SPR was performed on a Biacore 1000 instrument (Biacore). The substrate containing the SAM to be analyzed was mounted in a SPR cartridge as previously described (Sigal, G. B.; Bamdad, C.; Barberis, A.; Strominger, J. Whitesides, G. M., *Anal. Chem.*, Vol. 68, pp. 490-497, 1996; and Sigal, G. B.; Mrksich, M.; Whitesides, G. M., *Langmuir* Vol. 13, pp. 2749-2755, 1997). Our SPR protocol for measuring the adsorption of protein to SAMs consisted of: (i) flowing a solution of sodium dodecylsulfate (40 mM in PBS) over the SAM surface for 3 min followed by rinsing the surface with a solution of PBS buffer for 10 minutes; (ii) flowing PBS buffer for 2 min, then substituting the flow with a solution of protein (1 mg/mL in PBS) for 30 min and finally injecting PBS buffer for an additional 10 min, (e.g. FIG. 3). The flow rate used for all experiments was 10 μL/min.

% ML is defined according to equation 1. The smallest value of %ML that can be detect reliably is 0.2%; this number corresponds to approximately 10 RU. The quantity of adsorbed protein measured at different positions on the same sample or on samples that were prepared by following the same protocol on different days varied by ca. 5% (relative error).

Syntheses.

(2,3,4,5,6,-Pentahydroxyhexyl)carbamic acid tert-butyl ester (($CH_3)_3COC(O)NHCH_2(CH(OH))_4CH_2OH$).

1-Amino-1-deoxy-D-sorbitol (2.80 g, 15.4 mmol) was added to a solution of di-tert-butyl dicarbonate (3.40 g, 15.5 mmol) in DMF (30 mL) and the resulting mixture was stirred at 0° C. for 3 h, followed by stirring at ambient temperature for 16 h. The resulting solution was concentrated in vacuo to afford ($CH_3)_3COC(O)NHCH_2(CH(OH))_4CH_2OH$ as a colorless oil (4.50 g, 99%). This compound was used without further purification.

In this Example, an amine (HNRR') containing the functional group of interest (R') is allowed to react with a SAM presenting interchain carboxylic anhydride groups on its surface (see FIG. 1). This reaction generates a "mixed" SAM which comprises an ~1:1 mixture of —CONRR' and $CO_2H/CO_2^-$ groups. The ease with which this class of mixed SAMs can be prepared by the anhydride method (relative to the synthesis of the functionalized alkanethiols $HS(CH_2)_nR'$ normally used for the preparation of single-component SAMs) makes this route efficient for screening work.

The adsorption of two proteins to these surfaces is reported here: fibrinogen, a large (340 kD) blood plasma protein that adsorbs strongly to hydrophobic surfaces, and lysozyme, a small protein (14 kD, pI=12) that is positively charged under the conditions of our experiment (phosphate buffered saline, PBS, pH 7.4). The adsorption of fibrinogen and lysozyme on the mixed SAMs were tested because the properties of these two proteins (size and pI) are very different. Fibrinogen is a large (MW=340 kDa for a tetrameric aggregate, pI=5.5) protein that adsorbs readily to hydrophobic and charged surfaces. Fibrinogen is structurally similar to the extracellular matrix protein fibronectin that is often used to coat surfaces to facilitate the adhesion of mammalian cells. Hence, SAMs that are inert to fibrinogen may also be useful in applications to cell patterning in which it is necessary to prevent the adhesion of mammalian cells to certain parts of the surfaces. Lysozyme is a small (MW=15 kDa, pI=10.9) protein that is often used as a model in studies of electrostatic adsorption, and it is positively charged under the conditions of this experiment (phosphate buffered saline, PBS, pH 7.4). The adsorption of lysozyme to the mixed SAMs that are described here depends at least in part on the exposure to the solution of the $CO_2H/CO_2^-$ groups that are formed from the reaction of an amine with the anhydride groups; the positively charged protein would be attracted electrostatically to a surface with exposed $CO_2^-$ groups. Fibrinogen is used as a model for "sticky" serum proteins; lysozyme is often used in model studies of electrostatic adsorption of proteins to surfaces. Since lysozyme has a substantial net positive charge (Zp=+7.5 at pH 7.4, 100 mM KCl), it allowed for the examinations of attractive electrostatic interactions with $CO_2^-$ groups on the surface. Results are shown in Table 1.

The functional groups used in this study resulted in mixed SAMs that ranged substantially in their tendency to adsorb protein. SAMs that present oligo(ethylene glycol)$_n$ (n=3-6) groups are currently the most protein resistant surfaces available. However, these chains are susceptible to autoxidation. But from a protein-resistant standpoint, oligo(ethylene glycol), groups represent the standard for judging new protein resistant surfaces. The adsorption of proteins of mixed SAMs is compared to that of a mixed SAM that presents a 1:1 mixture of tri(ethylene glycol) groups (—$COHN(CH_2CH_2O)_3H$) and —$CO_2H/CO_2^-$ groups (see Table 1).

TABLE 1

Characterization of mixed SAMs that present —CONR'R/—CO$_2$H groups.

| HNRR' | Fibrinogen | | | | Lysozyme | | | | Clog$^{pe}$ | $\theta_{co}^f$ sessile |
|---|---|---|---|---|---|---|---|---|---|---|
| | % ML$_{fib}$ 3 min$^a$ | 30 min$^b$ | dR/dt$_{on}^c$ | % Fib$_{off}$ $^d$ | % ML$_{lys}$ 3 min$^a$ | 30 min$^b$ | dR/dt$_{on}^c$ | % Lys off$^d$ | | |
| HN–N–CH$_2$CH$_2$–O–CH$_2$CH$_2$–OH (piperazine-ethoxyethanol) | 1.2 ± 0.1 | 3.7 ± 0.0 | 54 ± 10 | 1.8 ± 0.1 | 4.5 ± 0.0 | 27 ± 10 | 20 ± 2 | 110 ± 5 | −0.85 | |
| CH$_3$HN–CH$_2$CH$_2$–N(CH$_3$)$_2$ | 23 ± 4 | 40 ± 2 | 140 ± 40 | 13 ± 2 | 1.9 ± 0.1 | 14 ± 2 | 400 ± 200 | 300 ± 30 | −0.03 | 49 |
| H$_2$N–CH$_2$CH$_2$–N$^+$(CH$_3$)$_3$ Cl$^-$ | 17 ± 2 | 25 ± 4 | 300 ± 200 | 6.2 ± 1 | 3.5 ± 0.2 | 3.9 ± 0.7 | 140 ± 40 | 95 ± 7 | −4.40 | 31 |
| HN–N–CH$_3$ (N-methylpiperazine) | 8.2 ± 1 | 16 ± 0.2 | 50 ± 30 | 1.0 ± 0.2 | 1.1 ± 0.2 | 1.0 ± 0.4 | 60 ± 40 | 170 ± 20 | −0.24 | 49 |
| CH$_3$HN–CH$_2$CH$_2$–NHCH$_3$ | 4.4 ± 0.8 | 8.5 ± 0.0 | 77 ± 30 | 7.5 ± 0.4 | 4.3 ± 0.1 | 7.8 ± 0.0 | 110 ± 60 | 110 ± 5 | −0.63 | |
| HN(CH$_3$)$_2$ | 26 ± 6 | 54 ± 0.8 | 160 ± 30 | 24 ± 0.1 | 43 ± 16 | 80 ± 3 | 2400 ± 260 | 120 ± 1 | −0.80 | |
| HN–N–CHO (N-formylpiperazine) | 23 ± 1 | 39 ± 1 | 200 ± 50 | 10 ± 2 | 8 ± 0.3 | 12 ± 0.3 | 160 ± 50 | 73 ± 15 | −0.81 | 38 |
| HN–N–C(O)CH$_3$ (N-acetylpiperazine) | 17 ± 1 | 38 ± 0.2 | 120 ± 70 | 12 ± 2 | 7.8 ± 1 | 6.5 ± 0.2 | 440 ± 80 | 400 ± 5 | −1.23 | 45 |
| H$_2$N–CH$_2$CH$_2$–NH–C(O)CH$_3$ | 14 ± 1 | 40 ± 2 | 50 ± 5 | 13 ± 1 | 1.4 ± 0.0 | 5.4 ± 0.3 | 530 ± 120 | 580 ± 20 | −1.44 | |
| CH$_3$HN–CH$_2$CH$_2$–N(CH$_3$)C(O)CH$_3$ | 2.1 ± 0.3 | 12 ± 3 | 40 ± 10 | 15 ± 1 | 0.5 ± 0.2 | 3.8 ± 2 | 170 ± 30 | 330 ± 15 | −0.64 | 46 |
| H$_2$N–CH$_2$–C(O)NH$_2$ | 33 ± 3 | 58 ± 1 | 250 ± 80 | 6 ± 3 | 8.8 ± 1 | 30 ± 1 | 1200 ± 400 | 420 ± 10 | | |
| H$_2$N–CH$_2$–C(O)N(CH$_3$)$_2$ (H$_2$N(Gly)$_1$N(CH$_3$)$_2$) | 18 ± 0.5 | 33 ± 0.5 | 202 ± 80 | 19 ± 0.2 | 7.2 ± 1 | 15 ± 1 | 590 ± 270 | 350 ± 10 | −1.21 | |

TABLE 1-continued

Characterization of mixed SAMs that present —CONR'R/—CO$_2$H groups.

| HNRR' | Fibrinogen | | | | Lysozyme | | | | Clog$^{pe}$ | $\theta_{co}^{f}$ sessile |
|---|---|---|---|---|---|---|---|---|---|---|
| | % ML$_{fib}$ 3 min$^a$ | 30 min$^b$ | dR/dt$_{on}^{c}$ | % Fib$_{off}$ d | % ML$_{lys}$ 3 min$^a$ | 30 min$^b$ | dR/dt$_{on}^{c}$ | % Lys off$^d$ | | |
| H$_2$N(Gly)$_3$N(CH$_3$)$_2$ | 8 ± 1 | 22 ± 0.4 | 55 ± 40 | 21 ± 0.7 | 2.1 ± 1.5 | 8.8 ± 0.5 | 620 ± 130 | 630 ± 4 | −1.77 | |
| 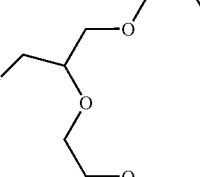 | 1.0 ± 0.0 | 9.1 ± 0.3 | 50 ± 23 | 28 ± 0.7 | 0.2 ± 0.1 | 2.4 ± 0.3 | 290 ± 130 | 740 ± 9 | −0.79 | |
| H(CH$_3$)N(Sar)$_1$N(CH$_3$)$_2$ | | | | | | | | | | |
| H(CH$_3$)N(Sar)$_3$N(CH$_3$)$_2$ | 0.7 ± 0.1 | 2.0 ± 0.1 | 60 ± 10 | | 0.6 ± 0.1 | 1.1 ± 0.3 | 70 ± 30 | | −0.75 | |
| H(CH$_3$)N(Sar)$_4$N(CH$_3$)$_2$ | 0.5 ± 0.0 | 1.7 ± 0.2 | 70 ± 20 | | 0.8 ± 0.1 | 1.5 ± 0.7 | 80 ± 40 | 70 ± 30 | −0.74 | |
| H(CH$_3$)N(Sar)$_5$N(CH$_3$)$_2$ | 0.6 ± 0.3 | 1.3 ± 0.1 | 50 ± 10 | | 0.8 ± 0.7 | 1.0 ± 0.2 | 50 ± 20 | 14 ± 4 | −0.72 | |
| 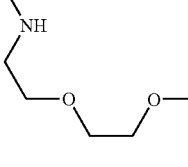 | 44 ± 0.9 | 59 ± 2.3 | 320 ± 110 | 9.7 ± 0.5 | 3.9 ± 0.3 | 9.6 ± 0.5 | 75 ± 40 | 14 ± 1.3 | −1.94 | |
| 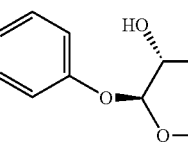 | 3.8 ± 0.7 | 11 ± 0.3 | 45 ± 20 | 9.6 ± 0.9 | 2.1 ± 0.4 | 6.0 ± 0.5 | 100 ± 50 | 72 ± 0.7 | −1.60 | |
| 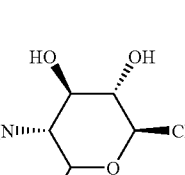 | 51 ± 1.8 | 67 ± 0.9 | 1200 ± 270 | 38 ± 0.8 | 27 ± 3.3 | 83 ± 2.3 | 1200 ± 270 | 78 ± 1.7 | −0.85 | |
| 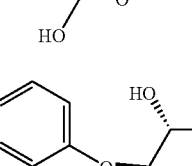 | 31 ± 0.7 | 55 ± 1.1 | 210 ± 120 | 11 ± 0.0 | 7.8 ± 0.2 | 25 ± 2.1 | 620 ± 280 | 330 ± 0.2 | −1.77 | |
| 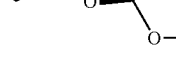 | 35 ± 5 | 49 ± 2.3 | 570 ± 250 | 17 ± 0.7 | 11 ± 1.5 | 30 ± 3.3 | 1300 ± 260 | 254 ± 10 | −0.85 | |

TABLE 1-continued

Characterization of mixed SAMs that present —CONR'R/—CO$_2$H groups.

| HNRR' | Fibrinogen | | | | Lysozyme | | | | Clog$^e$ | $\theta_{co}^f$ sessile |
|---|---|---|---|---|---|---|---|---|---|---|
| | % ML$_{fib}$ 3 min$^a$ | 30 min$^b$ | dR/dt$_{on}^c$ | % Fib$_{off}^d$ | % ML$_{lys}$ 3 min$^a$ | 30 min$^b$ | dR/dt$_{on}^c$ | % Lys off$^d$ | | |
| 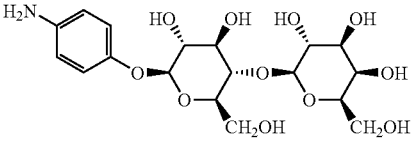 | 17 ± 1.4 | 32 ± 0.5 | 130 ± 80 | 7.4 ± 0.4 | 3.7 ± 0.1 | 9.3 ± 0.4 | 290 ± 120 | 190 ± 16 | −3.03 | |
| 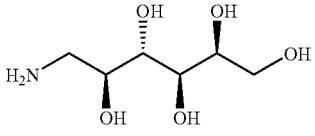 | 47 ± 12 | 68 ± 7 | 820 ± 500 | 4.8 ± 2 | 13 ± 7 | 20 ± 0.3 | 970 ± 400 | 290 ± 3 | −9.91 | |
| 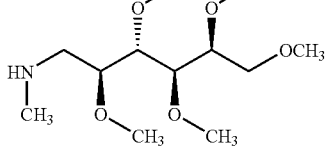 | 0.8 ± 0.5 | 2.9 ± 1.4 | 50 ± 50 | 18 ± 2 | 0.4 ± 0.4 | 6.1 ± 4 | 100 ± 70 | 17 ± 40 | −1.00 | |
| 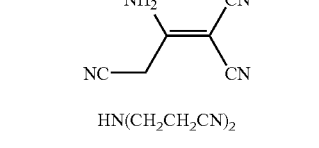 | 34 ± 1.1 | 58 ± 3 | 260 ± 70 | 11 ± 0.0 | 13 ± 0.3 | 28 ± 3.7 | 1900 ± 400 | 370 ± 20 | −1.72 | |
| HN(CH$_2$CH$_2$CN)$_2$ | 43 ± 1.0 | 58 ± 1.6 | 590 ± 240 | 20 ± 0.7 | 17 ± 1.0 | 40 ± 2.0 | 2700 ± 160 | 290 ± 8 | −0.66 | |
| HN(CH$_2$CN)$_2$ | 54 ± 3.8 | 73 ± 3 | 2200 ± 500 | 7.9 ± 0.9 | 36 ± 0.5 | 92 ± 0.3 | 2200 ± 500 | 110 ± 1 | −1.18 | |
| 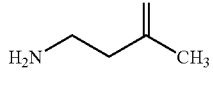 | 66 ± 0.3 | 74 ± 0.3 | 1400 ± 260 | 16 ± 1 | 31 ± 6 | 71 ± 5 | 2700 ± 400 | 150 ± 10 | −0.40 | 70 |
| 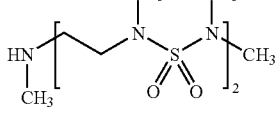 | 61 ± 0.1 | 80 ± 1 | 3000 ± 1000 | 9 ± 0.1 | 66 ± 4 | 100 ± 2 | 1500 ± 240 | 47 ± 3 | −0.01 | |
| H$_2$NC(CH$_2$CH$_2$CH$_2$OH) | 34 ± 2.2 | 57 ± 0.2 | 350 ± 220 | 14 ± 0.5 | 30 ± 0.6 | 73 ± 5 | 1400 ± 110 | 140 ± 2 | 2.63 | 70 |
| 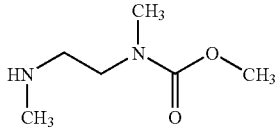 | 26 ± 0.2 | 58 ± 0.3 | 330 ± 70 | 20 ± 2 | 4.3 ± 0.2 | 43 ± 3 | 670 ± 50 | 150 ± 2 | 0.28 | 70 |
| H(CH$_3$)NCH$_2$CH(OCH$_3$)$_2$ | 16 ± 2 | 36 ± 1 | 510 ± 400 | 15 ± 4 | 4.6 ± 2 | 19 ± 5 | 740 ± 300 | 190 ± 2 | −0.85 | 70 |
| 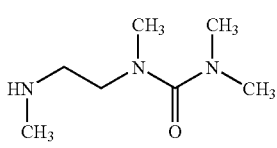 | 5.9 ± 0.2 | 25 ± 1 | 60 ± 30 | 15 ± 2 | 2.1 ± 0.2 | 11 ± 0.5 | 670 ± 50 | 160 ± 10 | −0.15 | 62 |

TABLE 1-continued

Characterization of mixed SAMs that present —CONR'R/—CO$_2$H groups.

| | Fibrinogen | | | | Lysozyme | | | | | |
|---|---|---|---|---|---|---|---|---|---|---|
| HNRR' | % ML$_{fib}$ 3 min[a] | 30 min[b] | dR/dt$_{on}$[c] | % Fib$_{off}$[d] | % ML$_{lys}$ 3 min[a] | 30 min[b] | dR/dt$_{on}$[c] | % Lys off[d] | ClogP[e] | θ$_{co}$[f] sessile |
| (structure: HN(CH$_3$)CH$_2$CH$_2$N(CH$_3$)P(O)(N(CH$_3$)$_2$)$_2$) | 0.8 ± 0.1 | 4.3 ± 0.6 | 120 ± 20 | 19 ± 1 | 0.2 ± 0.2 | 0.3 ± 0.2 | 70 ± 30 | 660 ± 15 | 0.44 | 63 |

[a] % ML$_{fib}$ is the percent of a monolayer of fibrinogen that adsorbed to a mixed SAM that presents —CONHR/—CO$_2$H groups. In this experiment, we assume that a monolayer of protein adsorbs to a mixed SAM that presents —CONH(CH$_2$)$_{10}$CH$_3$/—CO$_2$H groups after flowing a 1 mg/mL solution of fibrinogen over the surface for 3 minutes at 10 µL/second. % ML Lys is the equivalent measurement using lysozyme as the protein.
[b] Same as in [a] above with the exception that the protein solution was flowed over the surface for 30 minutes.
[c] dR/dt$_{on}$ (RU/sec) represents the maximum rate of adsorption of protein measured at the beginning of the association of the protein with the surfaces; we obtained the maximum initial rate of adsorption as the first derivative of the SPR signal with respect to time (at 0.5 second intervals). The rate decreased with increasing coverage of protein on the surface.
[d] % Fib$_{off}$ is the percent decrease in the amount of adsorbed protein during the 10 minute PBS wash of the surface that occurs after the injection of protein. It is relative to the amount of protein that is irreversibly adsorbed. % Lys$_{off}$ is the equivalent measurement using lysozyme as the protein.
[e] ClogP is the octanol/water partition coefficient calculated with the computer program MacLogP, see the experimental section.
[f] θ$_{co}$ is the contact angle in degrees of deionized water under cyclooctane.

Figure 3:
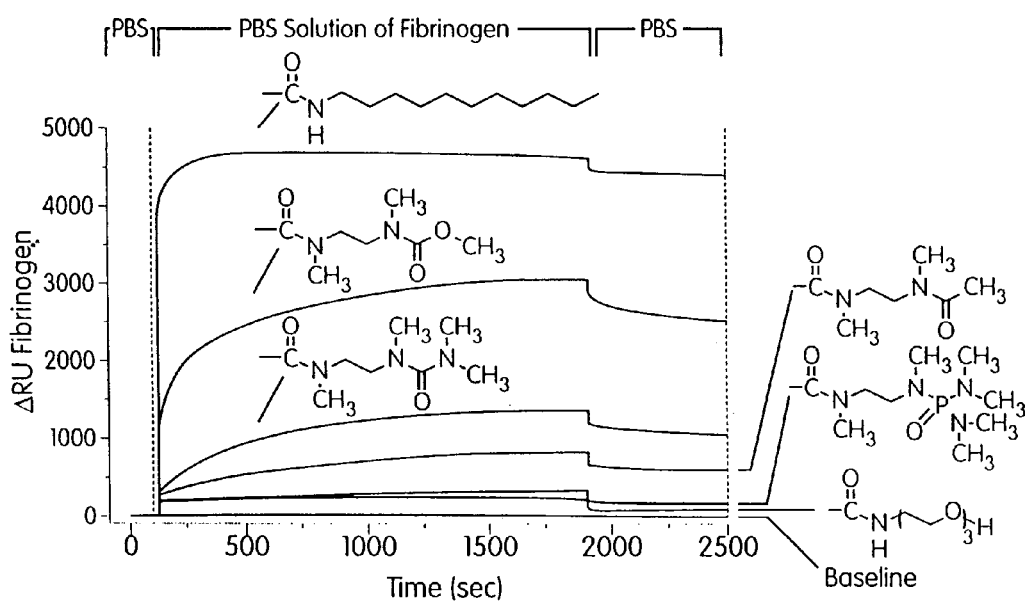
FIG. 3 shows a SPR sensorgram for the adsorption and desorption of fibrinogen to certain mixed SAMs, as labeled.

Based on this comparison, several terminal groups have been identified that show useful resistance to the absorption of proteins when presented on SAMS mixed ~1:1 with —CO$_2$H/CO$_2$—groups. Table 1 and FIG. 3 show the results of the screening of mixed SAMS. FIG. 3 shows a SPR sensorgram for the adsorption and desorption of fibrinogen to certain mixed SAMs, as labeled. "PBS" is the buffer. ΔRU was determined by subtracting the value of RU measured prior to the injection of protein from the value of RU measured 10 min. after the completion of the protein injection (see eq. 1 and accompanying discussion). Chemical chains of the present invention provide low ΔRU values compared to hydrophobic chains.

These terminal groups share several molecular characteristics, most particularly in that they do not contain hydrogen-bond donating groups. Other characteristics include: i) they contain polar functional groups; ii) they incorporate hydrogen bond accepting groups; and iii) they have an overall neutral charge.

Elimination of hydrogen bond donor groups appears to be a key structural element in surfaces that resist the adsorption of protein. Smaller amounts of proteins adsorbed to surfaces that presented compounds with NCH$_3$ and OCH$_3$ groups than to surfaces that presented their more polar analogues with NH and OH groups (Table 2). SAMs that presented OCH$_3$-terminated and OH-terminated oligo(ethylene glycol) groups adsorbed indistinguishable quantities of the two test proteins, but the quantities were too small to compare. It is concluded that mixed SAMs comprising a 1:1 mixture of —CONRR' and CO$_2$H/CO$_2$$^-$ groups provide a practical analytical system with which to screen functional groups for their ability to resist the adsorption of proteins. In addition, mixed SAM surfaces in themselves may afford a cheaper alternative to protein-resistant surfaces.

TABLE 2

Comparison of protein adsorption to mixed SAMs that present unmethylated and methylated functional groups, CONRR'.

| | % ML (R = H)[a] | |
|---|---|---|
| | % ML (R = CH$_3$) | |
| —CONRR' | fibrinogen | lysozyme |
| —CONRCH$_2$(CH(OR))$_4$CH$_2$OR | 23 | 3 |
| —CONRCH$_2$CON(R)$_2$ | 6 | 15 |
| —CONRCH$_2$CON(CH$_3$)$_2$ | 4 | 6 |
| —CONRCH$_2$CH$_2$NRCOCH$_3$ | 3 | 1.5 |
| —CONH(CH$_2$CH$_2$O)$_3$R[b] | 1 | 1 |

[a] These terms are defined by equation 1.
[b] Ref. 15

Thus, Table 1 identifies several useful alternatives to oligo(ethylene glycol): one —HN(CH$_3$)CH$_2$CON(CH$_3$)$_2$— is available commercially, and others—HN(CH$_3$)CH$_2$—(CH(OCH$_3$))$_4$CH$_2$O CH$_3$, HN(CH$_3$)CH$_2$CH$_2$N(CH$_3$)PO(N(CH$_3$)$_2$)$_2$), and HN(CH$_3$)CH$_2$CH$_2$N(CH$_3$)COCH$_3$— are straightforward to synthesize.

EXAMPLE 2

SAMs That Resist the Adsorption of Cells, Bacteria and Mammalian Cells

Figure 5:
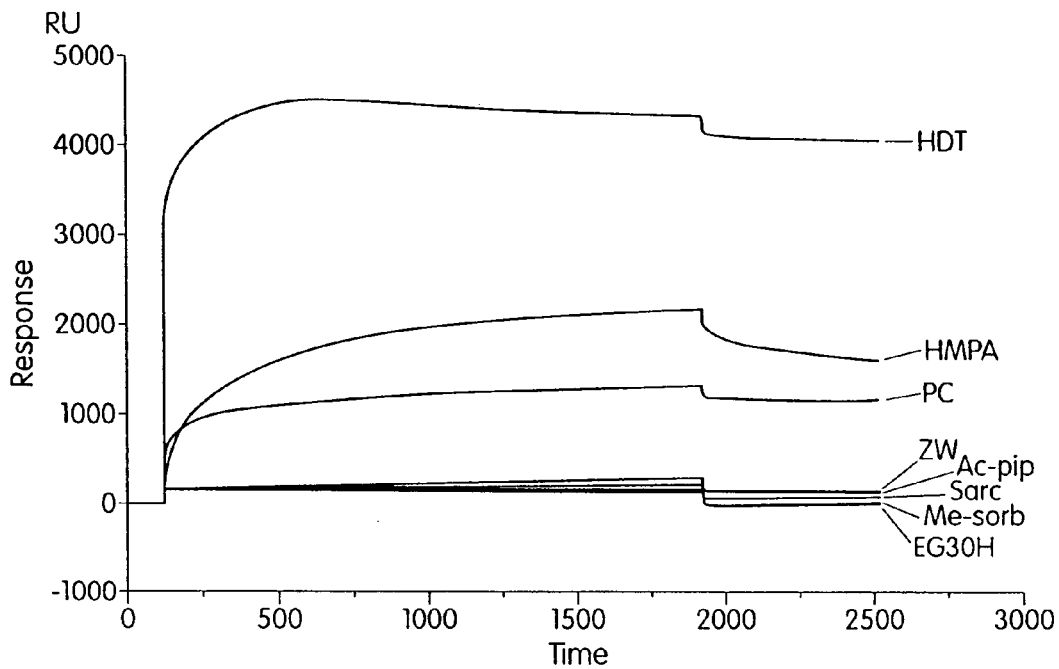
FIG. 5 shows SPR sensorgrams of chemical chains shown in FIG. 4.

This Example describes single-component SAMs which resist the adsorption of proteins from solution and the adhesion of *Staphylococcus epidermidis, Staphylococcus aureus*, and bovine capillary endothelial (BCE) cells. These surfaces present structurally diverse functional groups and allow forming structure property relationships between surfaces and their ability to resist the adsorption of proteins and the adhesion of cells. Structures of chemical chains in this Example are shown in FIG. 4. Resistance to the adsorption of proteins was screened and tested by SPR as described in Example 1. Results are shown in Table 3 and the SPR sensorgram of FIG. 5.

TABLE 3

Characterization of single-component SAMs that present groups that reduce the adsorption of protein from solution.
The results from the mixed SAMs that present the same groups is given for comparison.

| Entry No.[i] | RNH$_2$ or RSH | % ML 3 min[a] | % ML 30 min[b] | dR/dt$_{on}$[c] | % Fib off[d] | % ML 3 min[a] | % ML 30 min[b] | dR/dt$_{on}$[c] | % Lys off[d] | $\theta_{co}$[f] sessile |
|---|---|---|---|---|---|---|---|---|---|---|
| 1a | [HMPA-ethyl-amide-(CH$_2$)$_{10}$SH structure] | 13 ± 0.2 | 37 ± 2 | 83 ± 40 | 29 ± 0.4 | 4.5 ± 0.1 | 17 ± 0.3 | 330 ± 110 | 240 ± 2 | |
| 1b | [HMPA-ethyl-NHCH$_3$ structure] | 0.8 ± 0.1 | 4 ± 0.6 | 120 ± 20 | 19 ± 1 | 0.2 ± 0.2 | 0.3 ± 0.2 | 70 ± 30 | 660 ± 15 | 63 |
| 2a | [diacetyl piperazine (CH$_2$)$_{15}$SH structure] | 0.7 ± 0.0 | 2.2 ± 0.1 | 22 ± 10 | 6.8 ± 5 | 0.8 ± 0.3 | 0.8 ± 0.2 | 100 ± 10 | 110 ± 0 | |
| 2b | [acetyl piperazine NH structure] | 17 ± 1 | 38 ± 0.2 | 120 ± 70 | 12 ± 2 | 8 ± 1 | 7 ± 0.2 | 440 ± 80 | 400 ± 5 | 45 |
| 3a | HOEG$_3$(CH$_2$)$_{11}$SH (reference surface) | 0.2 | 0.2 | | | 0.2 | 0.2 | | | |
| 3b | H(OCH$_2$CH$_2$)$_3$NH$_2$ | 1 ± 0.2 | 2 ± 0.5 | 30 ± 15 | 11 ± 6 | 1 ± 0.2 | 1 ± 0.2 | 85 ± 50 | 240 ± 10 | 50 |
| 4a | [permethylated sorbitol-(CH$_2$)$_{10}$SH structure] | 0.2 ± 0.1 | 0.7 ± 0.1 | 30 ± 14 | 66 ± 5 | 0.5 ± 0.0 | 0.5 ± 0.2 | 29 ± 20 | 7 ± 0 | |
| 4b | [permethylated sorbitol NH structure] | 0.8 ± 0.5 | 2.9 ± 1.4 | 50 ± 50 | 18 ± 2 | 0.4 ± 0.4 | 6.1 ± 4 | 100 ± 70 | 17 ± 40 | |
| 5a | (CH$_3$)$_2$N(Sar)$_3$—NHCO(CH$_2$)$_{15}$SH | 0.7 ± 0.1 | 2.0 ± 0.0 | 24 ± 8 | 5.7 ± 5 | 1.8 ± 0.2 | 2.0 ± 0.7 | 33 ± 8 | 18 ± 0 | |
| 5b | (CH$_3$)$_2$N(Sar)$_3$N(CH$_3$)H | 0.7 ± 0.1 | 2.0 ± 0.1 | 60 ± 10 | | 0.6 ± 0.1 | 1.1 ± 0.3 | 70 ± 30 | | |

[i]The symbols used have been defined in Table 1.

Adhesion of Bacteria.

The number of viable colonies that attached to our homogeneous SAMs is measured by removing them from the surfaces of the substrates by sonication, growing them in media for a fixed amount of time, and counting them by determining their optical density.

Figure 6:
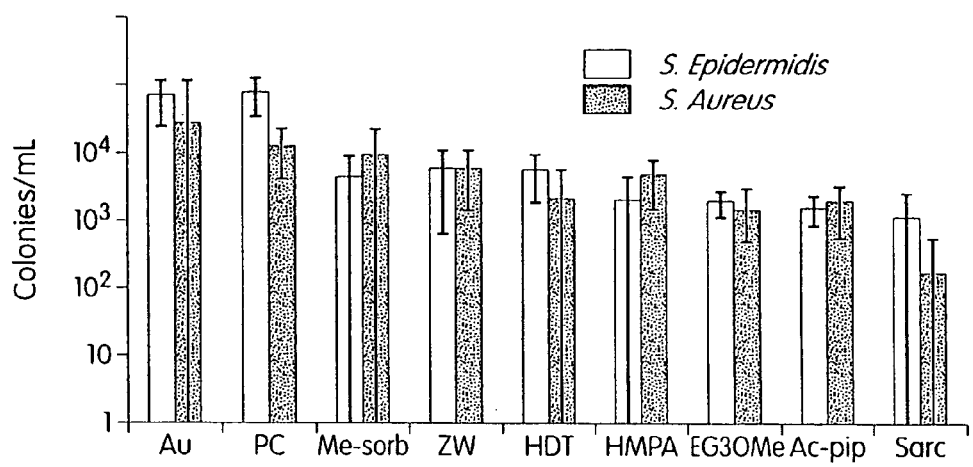
FIG. 6 shows a plot of the average number of bacteria bound to each substrate surface for chemical chains shown in FIG. 4.

SAMs that present oligo(N-methyl glycine) and acetyl piperazine derivatives resisted the adhesion of both strains of bacteria more than SAMs that presented EG$_3$OCH$_3$ groups (FIG. 6). A quantity representative of the average number of bacteria bound to each substrate surface is plotted on the Y axis. Error bars are the standard deviation of the experiments that were performed in triplicate. The experiments were repeated on two separate days with similar results. FIG. 6 shows a plot of only one set of results. SAMs that present phosphoramide derivatives, e.g., HMPA, permethylated sorbitol, and the intramolecular zwitterion (—CH$_2$N$^+$(CH$_3$)$_2$CH$_2$CH$_2$CH$_2$SO$_3$) resisted the adhesion of bacteria in a manner comparable to SAMs that presented EG$_3$OCH$_3$. SAMs that present a derivative of phosphoryl choline (PC) were not resistant to the adhesion of bacteria; the number of attached bacteria that was measured on PC surfaces was similar to the number measured on the surface of bare gold. This result is clearly consistent with the correlation between the amount of protein adsorption and the numbers of attached bacteria, and it may also be explained by the fact that the membranes of these bacteria present many phosphoryl choline derivatives.

Attachment of Mammalian Cells.

Figure 7:
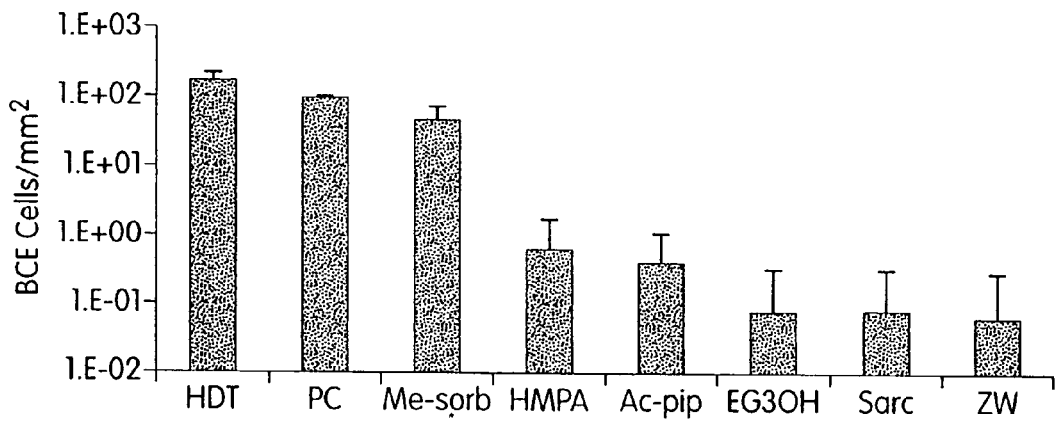
FIG. 7 shows a number of BCE cells that adhered per $mm^2$ of surfaces terminated with chains shown in FIG. 4.

The tested surfaces resisted the adhesion of cells in a manner comparable to SAMs that present tri(ethyleneglycol) groups except for SAMs that present derivatives of phosphoryl choline (FIG. 7). FIG. 7 shows a number of BCE cells that adhered per mm$^2$ of the surface. A number of cells that adhered to at least ten separate areas of a sample (1.26 mm$^2$ each) were measured. Similar results were obtained on two separate days; only one set of data is shown in FIG. 7. These results are consistent with the higher levels of adsorption of protein measured on surfaces formed with PC.

The few cells that adhered to the protein-resistant SAMs generally did not spread as much as those that adhered to single-component SAMs of hexadecanethiolates (HDT).

Correlation Between Protein Adsorption and Cell Adhesion.

Figure 8:
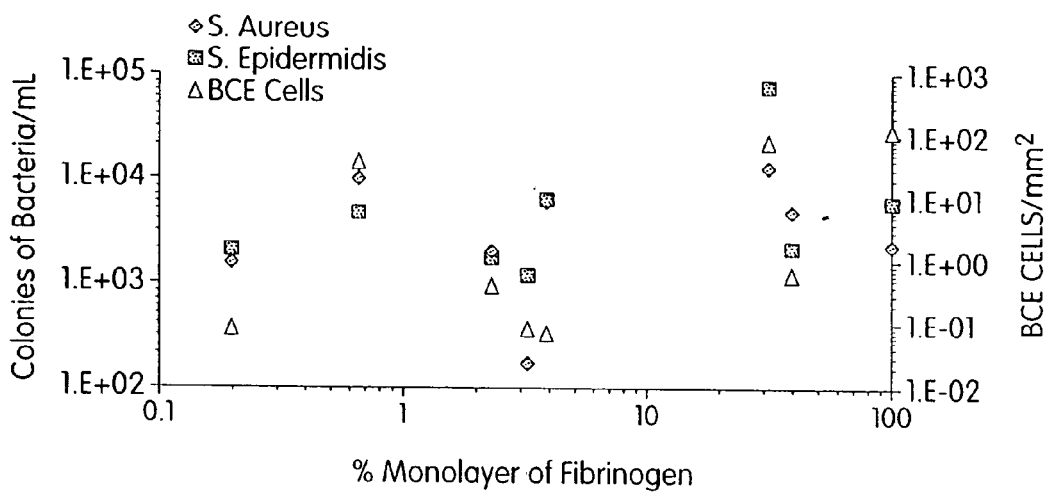
FIG. 8 shows a plot of the number of adhered BCE cells versus the amount of fibrinogen that adhered to the surface.

In general, the number of cells that attach to a surface correlates well with the amount of protein that adsorbs to the surface. However, the correlation is not linear. Although surfaces that present EG$_3$OH and EG$_3$OCH$_3$ groups are the most protein resistant surfaces available, they are not the most resistant to the adhesion of cells. FIG. 8 shows a plot of the number of adhered BCE cells vs. the amount of protein (% monolayer of fibrinogen) that adhered to that surface. The percentage of fibrinogen is plotted on a logarithmic scale for clarity. The number of bacteria that adhered to a SAM that presents oligo(N-methyl glycine) groups was one order of magnitude lower than on a SAM that presented EG$_3$OCH$_3$ groups (FIG. 6). Essentially no BCE cells attached to SAMs that presented tri(ethyleneglycol), tri(N-methyl glycine), and (—CH$_2$N+(CH$_3$)$_2$CH$_2$CH$_2$CH$_2$SO$_3$—) groups (FIG. 7); the amount of protein that adsorbed to these surfaces, however, was not identical. Specific structural features of these surfaces, along with their resistance to the adsorption of proteins, may help prevent cell adhesion.

EXAMPLE 3

Polymeric Thin Films that Resist the Adsorption of Cells, Bacteria and Mammalian Cells This Example describes the design and synthesis of thin, polymeric films that are covalently grafted on the surface of self-assembled monolayers (SAMs), and that resist the adsorption of proteins and the adhesion of bacteria. These surface films were prepared using a three-step process (FIG. 1). FIG. 1A: A single-component SAM of mercaptohexadecanoic acid was activated to present reactive interchain carboxylic anhydride groups on the surface. FIG. 1B: The reaction of this surface with polymeric amines generated a second surface presenting multiple amino groups in a thin, covalently grafted, polymer layer. FIG. 1C: The free amino groups on the immobilized polymers were acylated to introduce functional groups that resist the adsorption of proteins. The number of bacteria that adhered to the surface films that best resisted the adsorption of proteins was orders of magnitude lower than that measured on commercially available medical grade poly(urethane) and on so-called "bare" gold.

Figure 9:
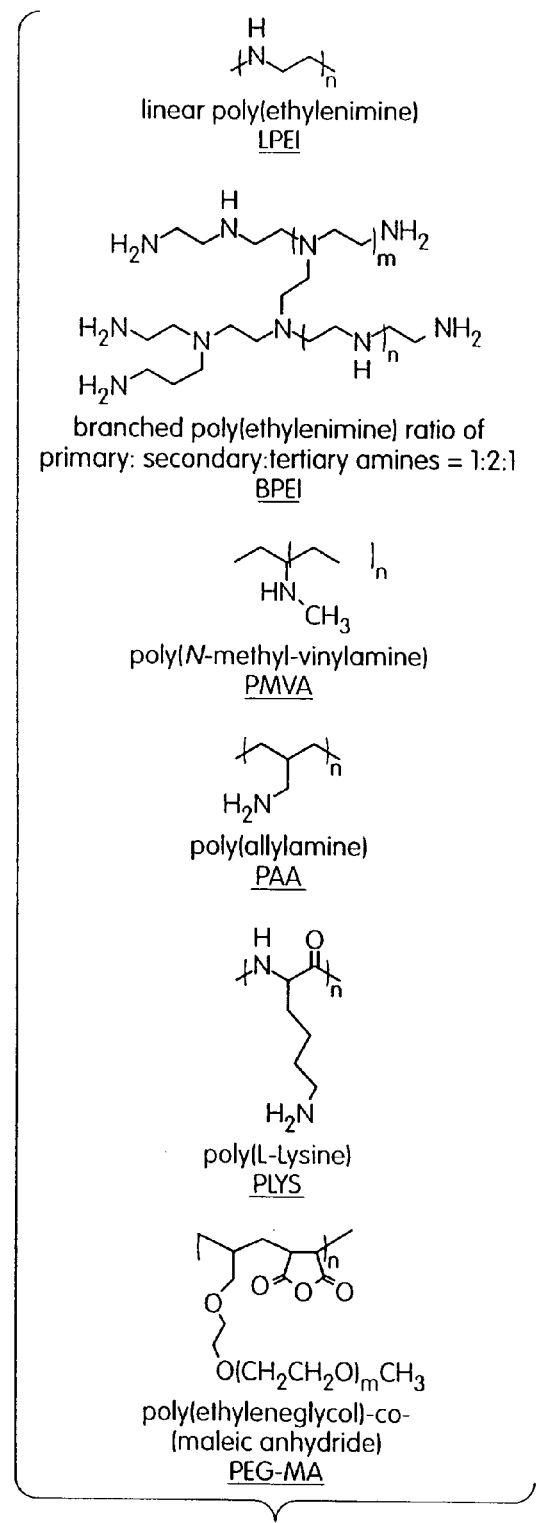
FIG. 9 shows various types of polyamines as well as a comparative PEG-MA.

Several types of polymeric amines were grafted onto a SAM that presented interchain carboxylic anhydride groups (FIG. 9). These grafted polymeric amines presented a high density of amino groups; these groups could be acylated with functional groups associated with inert surfaces. It is believed that the thin grafted films covers heterogeneities in the surface of the SAM/gold. The use of a SAM on gold as the substrate onto which to graft the polyamine films makes the system compatible with analysis of protein adsorption by SPR. These surfaces adsorbed <1% of a monolayer of fibrinogen and lysozyme, and reduced the adhesion of bacteria by three orders of magnitude relative to control surfaces.

Polyamines presenting —NH$_2$ and —NHCH$_3$ groups were used to evaluate the importance of hydrogen bond donor groups (e.g. LPEI, PMVA, PAA, and PLYS, FIG. 9). The importance of crosslinking in the polymer film was observed by comparing BPEI to LPEI.

Materials.

All chemicals used were reagent grade unless stated otherwise. Fibrinogen (from bovine plasma, F8630), lysozyme (egg white, E.C. 3.2.1.17, L6876) and sodium dodecyl sulfate were purchased from Sigma (St. Louis, Mo.). Anhydrous toluene, anhydrous N-methyl-2-pyrrolidinone (NMP), 16-mercaptohexadecanoic acid, trifluoroacetic acid (TFA), trifluoroacetic anhydride (TFAA), acetyl chloride, methoxyacetyl chloride, lauroyl chloride, heptafluorobutyryl chloride, diglycolic acid chloride, bromo-acetic acid tert-butyl ester, triethylene glycol monomethyl ether, poly(ethylene glycol) monomethyl ether (M$_w$=350), tetrabutyl ammonium bromide, 2-(2-methoxyethoxy)acetic acid, 2-[2-(2-methoxyethoxy)ethoxy] acetic acid, 4-dimethylaminopyridine, linear poly(ethylenimine) (LPEI, pentaethylenehexamine M$_w$=232), LPEI (M$_w$≈423), poly(2-ethyl-oxazoline) (PEOX, M$_w$≈500,000 and M$_w$≈200,000), poly(allyl amine) (PAA, M$_w$≈70,000), and poly(L-lysine) (PLYS, M$_w$≈25,000) were purchased from Aldrich (Milwaukee, Wis.). Poly(N-methylvinylamine) (PNVA, M$_w$≈25,000) and LPEI (M$_w$≈25,000) were purchased from PolySciences, Inc (Warrington, Pa.). Anhydrous N,N-dimethyl formamide (DMF), triethylamine, acetic anhydride, and ethylene glycol were purchased from EM Science (Gibbstown, N.J.). Absolute ethanol was purchased from Pharmco Products (Brookfield, Conn.). 2-(2-methoxyethoxy)acetic acid chloride was synthesized as previously described. (Asakawa, M.; Brown, C. L.; Menzer, S.; Raymo, F. M.; Stoddart, J. F.; Williams, D. J. *J. Am. Chem. Soc.* 1997, 119, 2614-2627). Phosphate-buffered saline (PBS: 10 mM phosphate, 138 mM NaCl, and 2.7 mM KCl) was freshly prepared in distilled, deionized water and filtered through 0.22 µM filters prior to use. The $^1$H-NMR spectra were recorded at 400 MHz on a Bruker spectrometer. Chemical shifts are reported in parts per million referenced with respect to residual solvent (CHCl$_3$=7.26 ppm).

Preparation of SAMs.

SAMs were prepared by immersing the freshly e-beam evaporated gold substrates (24×50 mm) in a 2 mM solution of the appropriate alkanethiol in ethanol at room temperature overnight. These substrates were removed from the solution and rinsed with ethanol before being dried in a stream of nitrogen. Glass substrates that were used for SPR studies and for the measurement of the adhesion of *Staphylococcus aureus* and *Staphylococcus epidermidis* were coated with 1.5 mn of titanium and 38 nm of gold. The adhesion of *E. Coli* was measured with glass substrates coated with 50 nm of Ti and 100 nm of gold.

Formation of Interchain Anhydrides.

SAMs were prepared by immersing gold substrates prepared as described above in a 2 mM solution of 16-mercaptohexadecanoic acid in a mixture of ethanol, water, and acetic acid (85:10:5 v/v) at room temperature overnight. The substrates were removed from the solution, thoroughly rinsed with ethanol, and dried with a stream of nitrogen. The cleaned substrates were placed in a freshly prepared solution of 0.1 M trifluoroacetic anhydride (TFAA) and 0.2 M triethylamine in anhydrous DMF without stirring for 20 minutes at room temperature. The substrates were removed from the TFAA solution, rinsed with $CH_2Cl_2$ and dried in a stream of nitrogen (Yan, L.; Marzolin, C.; Terfort, A.; Whitesides, G. M., *Langmuir*, Vol. 13, pp. 6704-6712, 1997).

Grafting polymers on SAMs and functionalization.

SAMs with terminal interchain carboxylic anhydride groups were used immediately by covering them with the appropriate solution of polymeric amine for 20 min (Yan, L.; Huck, W. T. S.; Zhao, X. -M.; Whitesides, G. M., *Langmuir*, Vol. 15, pp. 1208-1214, 1999). Solutions of polymers were 0.5% (w/v); LPEI polymers and PMVA were dissolved in NMP, BPEI polymers were dissolved in isopropyl alcohol, and PAA and PLYS were dissolved in buffer at pH=10. The polymer solution should not be contacted with the unfunctionalized side of the glass support. Contamination of the back of the substrate with polymer interfered with the optical interface of the SPR instrument. The substrates were then rinsed thoroughly with ethanol, dried in a stream of nitrogen, and immersed in a solution of $RCH_2COCl$ (0.3 mM), triethylamine (0.3 mM) and 4-dimethylaminopyridine (0.01 mM) in $CH_2Cl_2$ at 35° C. for 1 hour. The substrates were removed from the solution of acid chloride, rinsed thoroughly with ethanol, and dried in a stream of nitrogen. PEG-MA was grafted to surface-bound LPEI from an aqueous solution (1% w/w) for 30 min.

Surface Plasmon Resonance Spectroscopy.

A Biacore 1000 SPR instrument was used. The substrates to be analyzed were mounted on a modified SPR cartridge as described previously (Mrksich, M.; Sigal, G. B.; Whitesides, G. M., *Langmuir*, Vol. 11, pp. 4383-4385, 1995). The adsorption of proteins to SAMs was measured by: (i) flowing a solution of sodium dodecylsulfate (40 mM in PBS) over the SAM surface for 3 min followed by rinsing the surface with a solution of PBS buffer for 10 minutes; (ii) flowing PBS buffer for 2 min, then substituting the flow with a solution of protein (1 mg/mL in PBS) for 30 min and finally injecting PBS buffer for an additional 10 min. The flow rate used for all experiments was 10 μL/min.

In vitro Adhesion Model For *Staphylococcus epidermidis* and *Staphylococcus aureus*.

Functionalized gold substrates on 18 mm² glass coverslips (and bare gold) were rinsed in 100% ethanol immediately before use and placed in sterile 100×15 mm polystyrene dishes (Fisher). An inoculum of either *Staphylococcus epidermidis* M187 or *Staphylococcus aureus* MN8MUC (100 μL of a 2.5×10⁸/mL suspension) was added to the Petri dish, and incubated at 37° C. for 30 min. The suspension was spread over the entire surface of the gold substrates with a sterile pipet tip. The gold-coated substrates were removed from the medium, washed five times in sterile PBS, and sonicated for five sec in 10 mL of trypticase soy broth (TSB) containing 0.05% Tween. The resulting suspension was diluted (10-fold or 0-fold) before being placed on agar plates at 37° C. overnight. The number of colonies were counted under a microscope to determine the density of colony forming units (cfu) in the suspension obtained from sonicating the gold coated samples (plotted quantity). Each sample surface was tested in triplicate, with the bare gold surfaces done in quadruplicate; the experiment was repeated on three different days.

In vitro adhesion model for *E. coli*.

The particular strain of *E. coli* (RB 128) used was isolated from patients suffering from urinary tract infections by Dr. Shaw Warren at Harvard Medical School. Bacteria were grown in tryptic soy broth to mid-log growth phase, which corresponded to an optical density of approximately 0.3 at 650 nm. Bacteria were washed three times using phosphate buffered saline (PBS) solution (pH=7.4). During each washing step, 10 mL of PBS buffer were added to the test tube containing the bacteria followed by centrifugation at 3000 rpm for 10 min. The gold-coated substrates were placed vertically in a dish containing 200 mL of PBS buffer solution. The appropriate amount of the suspension of bacteria was added to the solution to adjust the bacterial concentration to 1×10⁵ bacteria/mL. The dish containing the substrates and the suspension of bacteria was placed in a shaker with the water-bath maintained at 37° C. After 1 h, the substrates were removed from the suspension of bacteria and washed using PBS buffer solution (3×200 mL). After drying each substrate under a gentle stream of nitrogen, it was contacted to agarose-coated plates. The substrate remained in contact with the agarose gel for 20-30 sec, and it was then lifted from the gel. After incubating the gel for 8 h at 37° C. the number of colony-forming units (cfa) were counted. The results are averages from five experiments using four different batches of *E. Coli*. Polyurethane (PU, Tecoflex, Thermedics Inc.) was used as a control.

Preparation of LPEI.

LPEI ($M_w \approx 250{,}000$ and $M_w \approx 100{,}000$) were prepared by the acid hydrolysis of PEOX ($M_w \approx 500{,}000$ and $M_w \approx 200{,}000$) with sulfuric acid followed by neutralization with NaOH and recrystallization from deionized water according to the procedure of Warakomski et al. (Kokufuta, E.; Suzuki, H.; Yoshida, R.; Yamada, K.; Hirata, M.; Fumitake, K., 1998, Vol. 14, pp. 788-795, 1998; Saegusa, T.; Ikeda, H.; Fujii, H., *Polym. J.*, Vol. 3, 1972; and Warakomski, J. M.; Thill, B. P., *J. Polym. Sci., Polym. Chem. Ed.*, Vol. 28, p. 3551, 1990). The ¹H NMR and ¹³C NMR spectra both showed only one signal. This observation suggested that the LPEI obtained was completely hydrolyzed.

Procedure 1: 2-[2-(2-Methoxy-ethoxy)ethoxy]acetic acid Chloride (1).

Oxalyl chloride (100 g, 0.78 mol) was added dropwise over 1 h to a solution of 2-[2-(2-methoxy-ethoxy)ethoxy]-acetic acid (90 mL, 0.59 mol) and pyridine (0.1 mL, 1 mmol) in anhydrous toluene (250 mL) and the resulting solution was stirred at ambient temperature for 48 h. The reaction solution was concentrated in vacuo to afford $CH_3(OCH_2CH_2)_2CH_2OCH_2COCl$ as a slightly yellow oil (120 g, 96%). This compound was used without any further purification.

Procedure 2: {2-[2-(2-Methoxy-ethoxy)-ethoxy]-ethoxy}acetic acid tert-butyl ester (2a)

Bromoacetic acid tert-butyl ester (20 mL, 0.14 mol), was added over a 10 min period to a rapidly stirred mixture of triethylene glycol monomethyl ether (20 mL, 0.13 mol), tetrabutyl ammonium bromide (20 g, 0.062 mol), toluene (100 mL) and KOH (50% w/w, 100 mL), and the resulting heterogeneous reaction mixture was stirred at 0° C. for 10 min. The reaction mixture was warmed to ambient temperature and stirred for 1 h. Water (100 mL) was added and the organic layer was separated. The organic layer was washed with saturated aq. $NH_4Cl$ (2×100 mL), saturated aq. $NaHCO_3$ (100 mL), brine (100 mL), and dried over anhydrous $MgSO_4$. The solution was concentrated in vacuo and the residue was loaded onto a silica gel gravity column (200 g) and eluted with ethyl acetate to afford $CH_3(OCH_2CH_2)_3CH_2OCH_2CO_2C(CH_3)_3$ as a colorless oil (420 g, 12%).

Procedure 3: {2-[2-(2-Methoxy-ethoxy)-ethoxy]-ethoxy}acetic acid (2b).

TFA (6 mL) was added to a solution of {2-[2-(2-methoxy-ethoxy)-ethoxy]-ethoxy}-acetic acid tert-butyl ester (4.2 g, 15 mmol) in $CH_2Cl_2$ (24 mL) and the resulting solution was stirred for 3 h at ambient temperature. The solution was concentrated in vacuo to afford $CH_3(OCH_2CH_2)_3CH_2OCH_2CO_2H$ (3.3 g, 99%) as a slightly yellow oil.

{2-[2-(2-Methoxy-ethoxy)-ethoxy]-ethoxy}acetic acid chloride (2c).

$(CH_3(OCH_2CH_2)_3CH_2OCH_2COCl)$ was prepared according to Procedure 1. Oxalyl chloride (3.6 mL, 0.041 mol); {2-[2-(2-methoxy-ethoxy)-ethoxy]-ethoxy}-acetic acid (3.3 g, 0.15 mol); pyridine (0.1 mL, 1 mmol) and anhydrous toluene (10 mL) to give $CH_3(OCH_2CH_2)_3CH_2OCH_2COCl$ as yellow oil (3.5 g, 99%). This compound was used without any further purification.

Poly(ethylene glycol) monomethyl ether-acetic acid tert-butyl ester (3a).

$(CH_3(OCH_2CH_2)_{5-7}CH_2OCH_2COOC(CH_3)_3)$ was prepared according to Procedure 2. Bromo-acetic acid tert-butyl ester (20 mL, 0.14 mol), poly(ethylene glycol) monomethyl ether (20 mL, 0.13 mol, $M_n$=350), tetrabutyl ammonium bromide (20 g, 0.062 mol), toluene (100 mL) and KOH (50% w/w, 100 mL) to give $CH_3(OCH_2CH_2)_n CH_2OCH_2CO_2C(CH_3)_3$ (n=5-7) as a colorless oil (10 g, 40%).

Poly(ethylene glycol) monomethyl ether-acetic acid (3b).

$(CH_3(OCH_2CH_2)_{5-7}-CH_2OCH_2COOH)$ was prepared according to Procedure 3. TFA (10 mL), $CH_3(OCH_2CH_2)_n CH_2O CH_2CO_2C(CH_3)_3$ (n=5-7) (10 g, 24 mmol) and $CH_2Cl_2$ (30 mL) to give $CH_3(OCH_2CH_2)_n CH_2OCH_2CO_2H$ (8.8 g, 99%) as a colorless oil.

Poly(ethylene glycol) monomethyl ether-acetic acid chloride (3c).

$(CH_3(OCH_2CH_2)_{5-7}CH_2OCH_2COCl)$ was prepared according to Procedure 1. Oxalyl chloride (3.6 mL, 0.041 mol); $CH_3(OCH_2CH_2)_n CH_2OCH_2CO_2H$ (n=5-7) (8.8 g, 0.24 mol); pyridine (0.1 mL, 1 mmol) and anhydrous toluene (20 mL) to give $CH_3(OCH_2CH_2)_n CH_2OCH_2COCl$ as a yellow oil (9.0 g, 99%). This compound was used without any further purification.

Grafting Polymeric Amines to the Surface of SAMs.

Thin films of polyamine were attached to SAMs in the fashion described in FIG. 1.

Modification of Amino Groups with Acyl Chlorides.

Reactions with low molecular weight acyl chlorides (0.3 mM) were carried out in dichloromethane. Poly(ethylene glycol) (n=30) derivatives were presented at the surfaces of the grafted film by reacting the SAM/LPEI with poly (ethylene glycol)-co-poly(maleic anhydride) (PEG-MA) (Yan et al. acylated a SAM/BPEI layer with $CH_3(CH_2)_{15}COCl$ and found that the resulting surface had $\theta_a^{H_2O}=107°$; acylation with $CF_3(CF_2)_7COCl$ gave a surface with $\theta_a^{H_2O}=118°$. These values of $\theta_a^{H_2O}$ are consistent with the formation of a hydrophobic layer with properties comparable to those of a SAM of hexadecanethiolate ($\theta_a^{H_2O}=112°$). The similarity of the values of the advancing contact angles of water on these surfaces suggests that there are few exposed polar functionalities on the acylated BPEI, but it does not provide any other information about the density of these groups.).

Adsorption of Proteins to SAMs that present LPEI/COR, BPEI/COR, PAA/COR, PMVA/COR, and PLYS/COR.

Both proteins adsorbed to a mixed SAM formed from the reaction of $CH_3(CH_2)_{10}NH_2$ with a SAM that presents anhydride groups (Chapman, R. G.; Ostuni, E.; Yan, L.; Whitesides, G. M., *Langinuir*, Accepted, 2000); an almost indistinguishable result was obtained with a SAM of hexadecanethiolate (Mrksich, M.; Sigal, G. B.; Whitesides, G. M., *Langmuir*, Vol. 11, pp. 4383-4385, 1995).

SPR was performed as discussed in Example 1.

Derivatives of Oligo(EG)$_n$.

Figure 10:
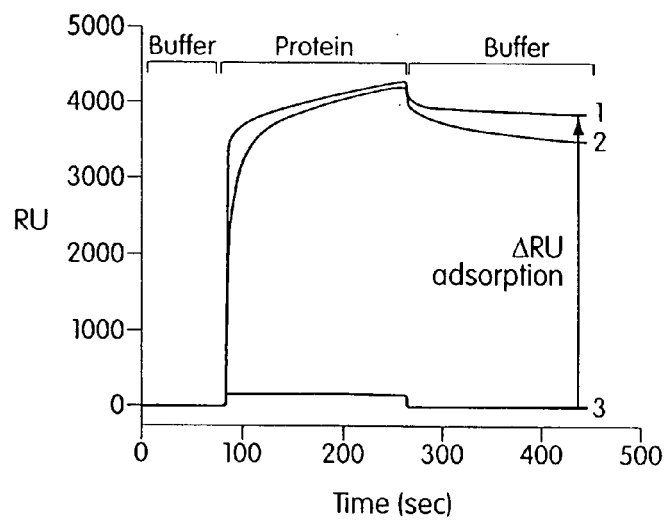
FIG. 10 shows sensorgrams for the adsorption of fibrinogen to different SAMs.

SAM/LPEI/COCH$_2$(EG)$_2$OCH$_3$ and SAM/PMVA/COCH$_2$(EG)$_2$OCH$_3$ adsorbed amounts of fibrinogen and lysozyme comparable to those adsorbed by single-component SAMs with (EG)$_3$OH groups (Table 4, FIG. 10).

TABLE 4

The percentages of monolayers of fibrinogen (% ML Fib) and Lysozyme (% ML Lys) that adsorbed to polymers (Scheme 1) grafted on SAMs.

| Entry | Polymer | MW (kDa) | Unfunctionalized[a] % ML | | ClCOCH$_3$[b] % ML | | ClCOCH$_2$(EG)$_2$OCH$_3$[b] % ML | |
|---|---|---|---|---|---|---|---|---|
| | | | Fib | Lys | Fib | Lys | Fib | Lys |
| 1 | LPEI | 0.23 | 79 | 15[c] | 2.8 | 0.4 | 0.0[g] | 0.2 |
| 2 | LPEI | 0.42 | | | 5.9[d] | 2.0[d] | 0.4 | 0.0[g] |
| 3 | LPEI | 25 | 87 | 19 | 1.9 | 3.3[d] | 0.4 | 0.5[d] |
| 4 | LPEI | 100 | | | 0.9 | 1.1 | 0.6 | 0.3[d] |
| 5 | LPEI | 250 | | | 0.4 | 0.5 | 0.3 | 0.3 |
| 6 | BPEI | 0.8 | | | 1.5 | 0.5 | 1.0[d] | 0.0 |
| 7 | BPEI | 25 | 82 | 27 | 2.2 | 0.9 | 0.2 | 0.3 |
| 8 | BPEI | 750 | | | 1.1 | 0.3 | 0.3 | 0.0[g] |
| 9 | PMVA | ~200 | 117[e] | 18 | 0.5 | 0.3 | 0.3 | 0.4 |
| 10 | PAA | 70 | 99[f] | 88 | 30[f] | 7.2[f] | 4.5[d] | 2.3 |
| 11 | PLYS | 25 | 91[f] | 29 | 71[f] | 50[c] | 0.7[d] | 0.3 |

The listed polymers (Scheme 1) were reacted with a SAM that presented interchain carboxylic anhydride groups and functionalized further with the acyl chlorides listed in the first row of the table. "Unfunctionalized" in the first row refers to polymers that were not reacted with acyl chlorides. The surfaces were exposed to a solution of protein (1 mg/mL) for 3 min, and then to buffer for 10 min. The reported values are percentages of the amount of protein that adsorbed to a mixed SAM formed by the reaction of an anhydride SAM with $CH_3(CH_2)_{10}COCl$.
[a]The standard deviation (SDEV) in all measurements in this section was ≦5, unless specified otherwise.
[b]The standard deviation in all measurements in this section was ≦0.3 unless specified otherwise.
[c]SDEV ≦17.
[d]SDEV ≦1.
[e]Some surfaces allow the adsorption of more protein than the hydrophobic standard used here; this happens rarely
[f]SDEV ≦8.
[g]The measured value is experimentally insignificant (<0.2%).

FIG. 10 shows sensorgrams for the adsorption of fibrinogen to different SAMs. The surface of LPEI-CO(CH$_2$)$_{11}$CH$_3$ (25 kDa) absorbs nearly a full monolayer of protein (curve 1). A mixed SAM that presents unfunctionalized LPEI also absorbs almost a full monolayer of protein (curve 2). Acetylation of the SAM with CH$_3$O(CH$_2$CH$_2$O )$_2$CH$_2$COCl generates a surface that resists the adsorption of protein (curve 3). The amount of adsorbed protein is defined as the difference in signal between the end of the experiment and the beginning of the injection of protein, $\Delta$RU. The percentages of adsorbed proteins were determined as in equation 1, by dividing the values of $\Delta$RU measured on the polymer coatings by the value of $\Delta$RU measured on a mixed SAM prepared by the reaction of an interchain anhydride with CH$_3$(CH$_2$)$_{10}$NH$_2$.

Thin films of LPEI (25 kDa) grafted on SAMs resisted the adsorption of protein to the same extent when they were functionalized with CH$_3$O(EG)$_n$CH$_2$COCl with n$\geq$2 (Table 5); this result is consistent with prior theories that high densities of short oligomers of ethylene glycol render surfaces inert.

TABLE 5

The percentages of monolayers of proteins that adsorbed to SAM/LPEI/COR.

| | | % ML | |
|---|---|---|---|
| Entry | ClCOR | Fib[a] | Lys[a] |
| 1 | Unacylated LPEI | 87 | 19 |
| 2 | ClOC(CH$_2$)$_{10}$CH$_3$ | 93 | 76[b] |
| 3 | ClOC(CF$_2$)$_3$CF$_3$ | 91 | 69 |
| 4 | ClOCCH$_2$OCH$_3$ | 0.3 | <0.2[c] |
| 5 | ClOCCH$_2$(OCH$_2$CH$_2$)$_1$OCH$_3$ | 0.3 | 0.3 |
| 6 | ClOCCH$_2$(OCH$_2$CH$_2$)$_2$OCH$_3$ | 0.4 | 0.5[d] |
| 7 | ClOCCH$_2$(OCH$_2$CH$_2$)$_3$OCH$_3$ | 0.2 | 0.2 |
| 8 | ClOCCH$_2$(OCH$_2$CH$_2$)$_{5-7}$OCH$_3$ | <0.2[c] | 0.2 |
| 9 | PEG-MA (14 kDa)[e] | <0.2[c] | 0.2 |

LPEI (25 kDa) was reacted with an anhydride SAM and then functionalized with the listed acyl chlorides (ClCOR). The determination of the percentages of adsorbed proteins and the experimental protocol used to measure the adsorption of protein are described in the footnotes to Table 1 and in the text.
[a]The standard deviation (SDEV) for entries 1-3 was $\leq$4. SDEV for entries 4-9 was <0.3, unless specified otherwise.
[b]SDEV = 11.
[c]We cannot measure less than 0.2%.
[d]SDEV = 0.7.
[e]The anhydride groups on the copolymer reacted with the free amines on LPEI.

Acetyl Groups.

The reaction of acetyl chloride with the surfaces covered with polyamines generated surfaces with a high density of acetamido groups (R$_2$NCOCH$_3$); these surfaces resisted the adsorption of protein relative to the grafted polymer film that was not acylated (Table 4). The amount of protein that adsorbed to acetylated films of LPEI was lower than that adsorbed to unfunctionalized films; this observation is consistent with previous studies indicating that SAMs that present secondary or primary amino groups adsorb more protein than structurally similar groups that present acetyl amide (NCOCH$_3$) groups. Acetylation of the grafted polyamines with acetic anhydride generated surfaces that adsorbed slightly larger amounts of fibrinogen than those acetylated with acetyl chloride. Polymer films grafted with —COCH$_2$(EG)$_2$OCH$_3$ groups adsorbed 1-10 times less protein than acetylated films (Table 4).

Unfunctionalized Polymers.

Proteins adsorbed to the unacylated thin films of the polyamines because they are positively charged (R$_3$N$^+$H); they also have a high density of hydrogen bond donor groups. The surfaces of SAMs coated with polymeric amines adsorbed from 1-8 times more fibrinogen than lysozyme (Table 4). It is probable that the partially positively charged films repelled the positively charged lysozyme (pI=11) and attracted the negatively charged fibrinogen (pI=5.5). pI refers to the pH at which the protein has no net charge. At values of pH below pI, the protein is positively charged.

Hydrophobic Groups.

The amounts of proteins that adsorbed to polymeric films acylated with hydrophobic groups such as CH$_3$(CH$_2$)$_{10}$COCl and CF$_3$(CF$_2$)$_3$COCl suggest that the surfaces were largely hydrophobic in character (Table 5). These results are consistent with the report of Yan et al. (Yan, L.; Huck, W. T. S.; Zhao, X. -M.; Whitesides, G. M., *Langmuir*, Vol. 15, pp. 1208-1214, 1999) that the advancing contact angles of water on films of BPEI acylated with CH$_3$(CH$_2$)$_{15}$COCl and CF$_3$(CF$_2$)$_7$COCl are comparable to those measured on SAMs of hexadecanethiolate.

Influence of the Structure of the Polymer on the Adsorption of Protein:

Molecular Weight.

The amount of protein that adsorbed to surfaces formed with LPEI/COCH$_3$ decreased slightly with increasing molecular weight of the polymer; the results obtained with BPEI/COCH$_3$ are generally consistent with that trend. One of the possible explanations for this observation is that the larger polymers are likely to cover both surface heterogeneities and the CO$_2^-$/CO$_2$H groups of the SAM more effectively than their lower molecular weight variants. The amount of protein that adsorbed to surfaces coated with SAM/LPEI/COCH$_2$(EG)$_2$OCH$_3$ was independent of the molecular weight of the polymer; this result is consistent with prior knowledge that surfaces covered with derivatives of ethylene glycol resist the adsorption of proteins.

Hydrogen Bond Donor Ability.

The functionalized polymer films that best resisted the adsorption of protein were obtained by grafting thin films of polymers composed strictly of secondary amine groups (LPEI, PMVA), and reacting these groups with ClCOR derivatives (R=CH$_3$, (EG)$_{n\geq 2}$OCH$_3$) or other ether derivative. Based on previous work, it is believed that the elimination of hydrogen bond donor groups from the films formed by reaction with an acyl chloride may contribute to the resistance of these materials to the adsorption of protein.

The acetylation of films of LPEI, BPEI, and PMVA transformed hydrogen bond donor groups (RR'NH) into groups that were exclusively hydrogen bond acceptors (R'RNCOCH$_3$), and resulted in surfaces that resist the adsorption of proteins. Acetylation of primary amino groups on films of PLYS and PAA generated secondary amido groups (HNCOR) that still had hydrogen bond donor groups; these surfaces adsorbed proteins.

Although the amount of protein that adsorbed to polyamines acylated with acetyl chloride depended on the structure of the polymer, the amount that adsorbed on polyamines acylated with ClCOCH$_2$(EG)$_2$OCH$_3$ did not. The oligo(ethylene glycol) derivatives probably screened the hydrogen bond donor and charged groups more effectively than the acetyl amide groups, in part because of their larger size.

Adhesion of *Staphylococcus epidermidis* and *Staphylococcus aureus* to Mixed SAMs Presenting LPEI/COR.

*Staphylococcus epidermidis* and *Staphylococcus aureus* cause 30-50% of the infections associated with in-dwelling devices. These strains adhere to the surfaces of host cells and artificial materials via a secreted layer of polysaccharides that is recognized by the bacterial adhesins. This assay determined the number of viable bacteria that adhered to the surface films after incubating a suspension of bacteria with the substrates for 30 min. The bacteria were removed from the surface of the substrate by sonication; the resulting suspension was incubated on agar plates overnight. The number of bacterial colonies on each plate was counted to determine the density of colony forming units (cfu/mL) found in the solution obtained after sonication of the substrates; this number is proportional to the number of bacteria that adhered to each substrate. Sonication left some bacteria on the surfaces, especially on the bare gold control; thus, the control numbers are artificially low.

Figure 11:
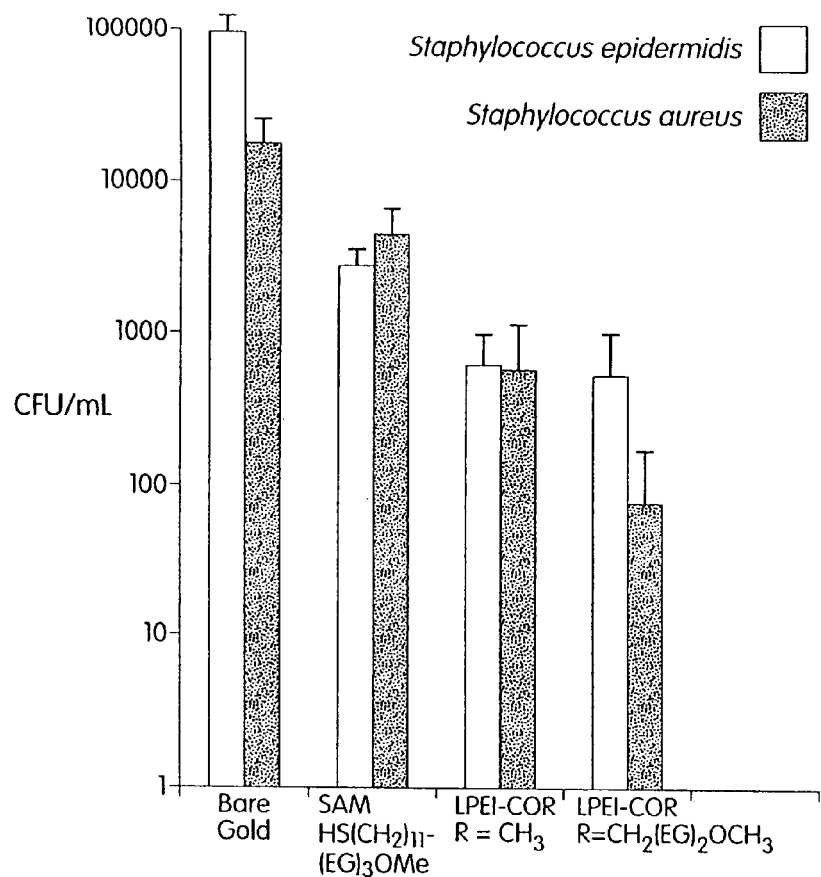
FIG. 11 shows the adhesions of S. epidermidis and S. aureus to various surfaces.

The smallest number of bacteria adhered to mixed SAMs presenting $LPEI/COCH_2(EG)_2OCH_3$; values that were ca. three orders of magnitude lower than on bare gold were measured, and ca. two orders of magnitude lower than on a SAM that presented $(EG)_3OCH_3$ groups (FIG. 11). FIG. 11 shows the adhesion of *Staphyloccus epidermidis* and *Staphylococcus aureus* to bare gold, a pure SAM of $HS(CH_2)_{11}EG_3OCH_3$, and mixed SAMs that present $LPEI-COCH_3$ and $LPEI-COCH_2(OCH_2CH_2)_2OCH_3$ (100 kDa). The quantity plotted on the y-axis represents the number of bacteria (colony forming units, cfu) that bound to each substrate. The error bars are the standard deviation of the measurements that were performed in triplicate. The experiments were performed on four separate days with similar results; for clarity, only one set of results are shown.

Adhesion of *E. Coli* to Mixed SAMs Presenting LPEI-COR.

Figure 12:
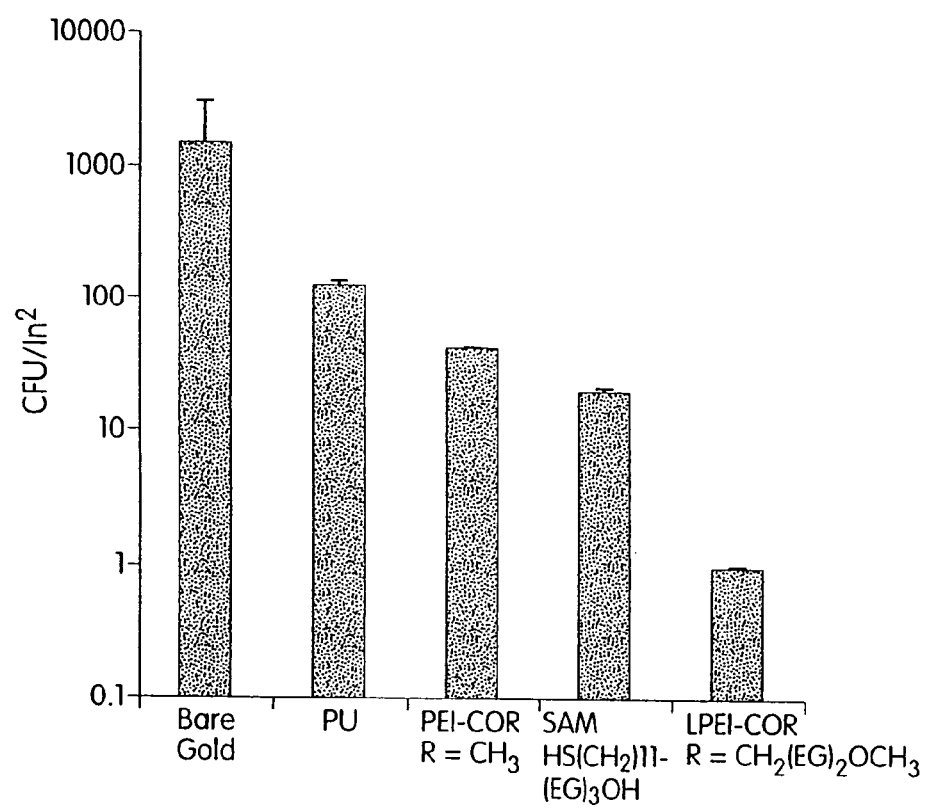
FIG. 12 shows the adhesion of E. Coli to various surfaces.

The strain of *E. Coli* that we tested was isolated from patients with urinary tract infections and was provided to us by Dr. Shaw Warren (Mass.General Hospital). The number of colony forming units (cfu's) that adhered to test substrates was measured by using an "imprint" assay. This assay was performed by contacting substrates covered with bacteria with agarose-coated plates, transferring bacteria from the gold substrates to agar plates, and counting cfu's after incubation (FIG. 12). The number of bacteria that adhered to the bare gold surface, however, was too high to allow accurate counting, and the reported value represents a lower limit.

The number of attached, viable bacteria was lowest for SAMs functionalized with $LPEI/COCH_2(EG)_2OCH_3$ (FIG. 12). FIG. 12 shows the adhesion of *E. Coli* to bare gold, medical grade poly(urethane), a pure SAM of $HS(CH_2)_{11}EG_6OH$ and mixed SAMs that present $LPEI-OCH_3$ and $LPEI-COCH_2(OCH_2CH_2)_2OCH_3$ (100 kDa). We plot the number of colony forming units per square inch. The value plotted for bare gold represents a lower limit; the number of bacteria that adhered on bare gold was too high to be determined accurately. The error bars are the standard deviation of the measurements. The experiments were performed on two separate occasions with similar results. For clarity, only one set of results is shown here.

Using $LPEI/COCH_3$ provided an improvement of two orders of magnitude over bare gold, and one order of magnitude over PU. This coating performed as well as a SAM terminated with $(EG)_6OH$ groups, but not as well as $SAM/LPEI/COCH_2(EG)_2OCH_3$.

$LPEI/COCH_2(EG)_2OCH_3$ and $LPEI/COCH_3$ resist the adsorption of proteins from solution almost as effectively as single-component SAMs that present oligo(ethylene glycol) derivatives. Some of the most protein resistant films reported here ($LPEI/COCH_3$, $PMVA/COCH_3$) were obtained without using derivatives of ethylene glycol. $SAM/LPEI/COCH_2(EG)_2OCH_3$ and $SAM/LPEI/COCH_3$ resisted the adhesion of bacteria in a manner comparable or superior to SAMs whose surface groups are $(EG)_nOR$ (n=3, 6; R=H, $CH_3$). The number of bacteria that adhered to these films (relative to the control surfaces of SAMs terminating in (EG), OR groups) depended on the strain of bacteria being examined. Although the mechanism of bacterial adhesion to surfaces is highly dependent on the strain, the results that we obtained with *E. Coli*, *Staphylococcus aureus*, and *Staphylococcus epidermidis* suggest that these films may show broad resistance to attachment of bacteria.

Grafting of Other Surfaces with Polymers.

This section demonstrates how other surfaces, such as polymer surfaces, can be grafted with PEI.

Polyurethane (PU) catheters and glass slides coated with PU from solution were functionalized with PEI to generate inert substrates. The polyurethane substrates were placed in a solution of toluene diisocyanate (1 mL) and stannous octanoate (100 μL) in anhydrous hexanes (100 mL). The reaction mixture was heated to 60° C. for 45 min and quickly rinsed in water. The polyurethane substrates were then immersed in a solution of BPEI (1% w/v in water) at 4° C. overnight. After rinsing with water, the polyurethane substrates were reacted with acyl chloride derivatives. Acetonitrile instead of methylene chloride was used as the solvent for the acetylation of the polyurethane catheters.

Acetylated polyamine coatings were attached to the surface of polydimethylsiloxane (PDMS) slabs to render them resistant to the adsorption of proteins. The PDMS was treated in a plasma oxidizer for 30 seconds to generate reactive groups at its surface such as hydroxyl groups. The PDMS substrate was then exposed to a trichloroalkylsilane terminated with an alkene functional group. The terminal alkene functional group was oxidized with $KMnO_4$ to generate carboxylic acid groups. The carboxylic acid groups were then converted to carboxylic anhydride groups. The subsequent grafting of the polyamine to this surface and the acylation of the polymer were performed as described in this Example.

EXAMPLE 4

Biospecific Binding of Carbonic Anhydrase

Figure 13:
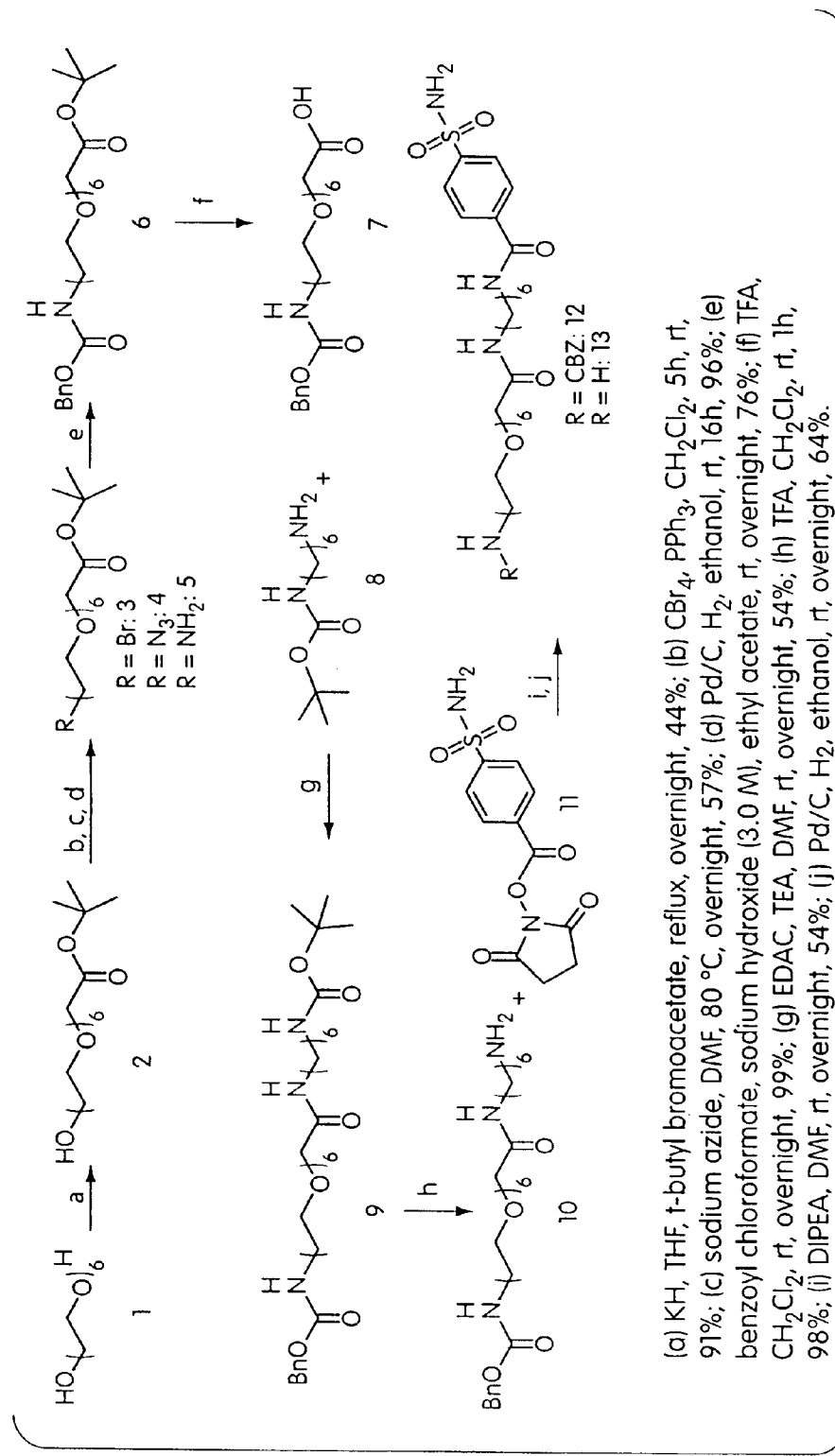
FIG. 13 shows a scheme for the preparation of compound 13.

A SAM that can recognize and adsorb CA biospecifically was prepared by reacting the anhydride groups (see FIG. 1) with a mixture of $H_2N(CH_2CH_2O)_6H$ and the benzene sulfonamide derived from $H_2N(CH_2CH_2O)_6CH_2CONH(CH_2)_6NHCOC_6H_4SO_2NH_2$ (compound 13) (FIG. 13). FIG. 13 shows a scheme for the preparation of compound 13.

Figure 14:
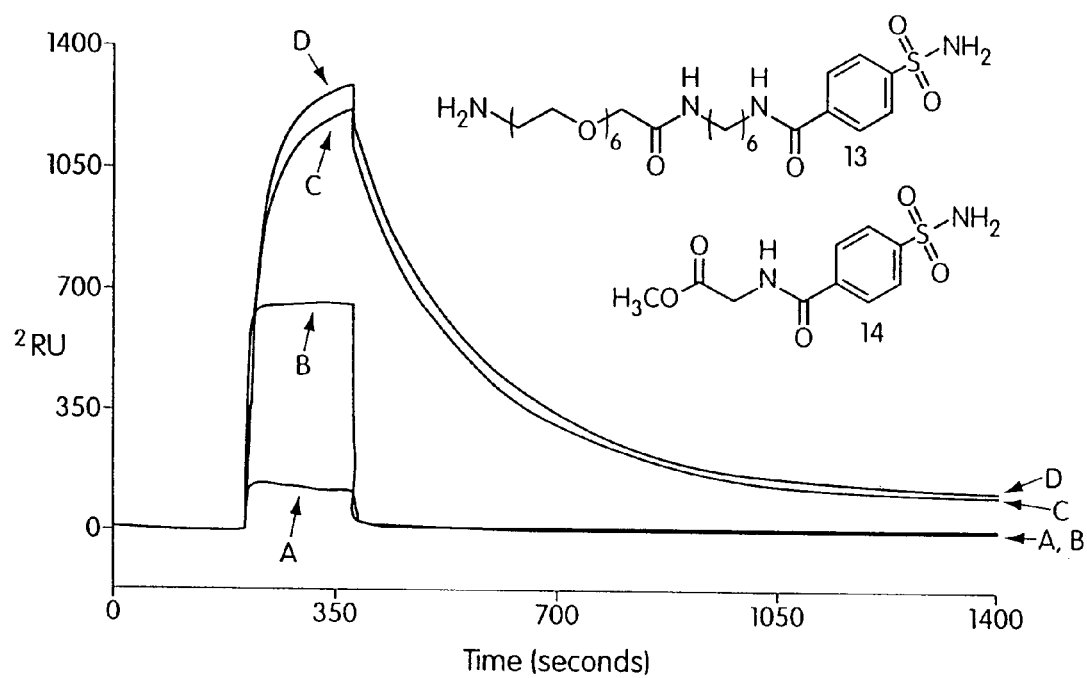
FIG. 14 shows an SPR sensorgram obtained for the adsorption and desorption of CA.

Attachment of Benzenesulfonamide to the Surface:

FIG. 14, plot C shows the SPR sensorgram obtained for the adsorption and desorption of CA (5 μM in phosphate buffered saline (PBS) buffer) to a mixed SAM that presents benzene sulfonamide 13 covalently immobilized on its surface. The binding of CA was largely reversible (>90%). Analysis of the rate of dissociation and association of CA from the mixed SAM presenting benzenesulfonamide groups resulted in a value of $k_{off}=0.0054$ s$^{-1}$ and a value of $k_{on}=13000$ M$^{-1}$s$^{-1}$, (Table 6).

TABLE 6

Thermodynamic and kinetic constants for binding of CA to benzene sulfonamide ligands. Entry 4 corresponds to the values determined by SPR in this paper.

$H_2N-SO_2-C_6H_4-CO-R$

| | R = | $k_{on}$ (M$^{-1}$s$^{-1}$) | $k_{off}$ (s$^{-1}$) | $K_d$ (μM) |
|---|---|---|---|---|
| 1 | —OH measured by capillary electrophoresis | a | a | 1.25 |
| 2 | —NH(CH$_2$)$_6$NHCOCH$_2$OEG$_6$(CH$_2$)$_{11}$S—/Au by co-adsorption of two thiols | 19000 | 0.0054 | 0.26 |
| 3 | —NH(CH$_2$)$_6$NHCOCH$_2$OEG$_6$(CH$_2$)$_{11}$S—/Au by coupling to a N-hydroxysuccinimidyl ester | 9400 | 0.0054 | 0.56 |
| 4 | —NH(CH$_2$)$_6$NHCOCH$_2$(OCH$_2$CH$_2$)$_6$NHCO(CH$_2$)$_{15}$S—/Au by reaction with carboxylic anhydride groups | 13000 | 0.0054 | 0.42 |
| 5 | Dextran-BIACORE | 7600 | 0.0052 | 0.68 |
| 6 | LPEI-1% ClCOCH$_2$OCH$_2$COCl, H$_2$NEG$_6$NH$_2$, BSANHS | 5200 | 0.011 | 2.2 |
| 7 | LPEI-1% ClCOCH$_2$OCH$_2$COCl, NHS activation, BSAEG$_6$NH$_2$ | 6000 | 0.0051 | 0.85 |
| 8 | LPEI-5% ClCOCH$_2$OCH$_2$COCl, H$_2$NEG$_6$NH$_2$, BSANHS | 5700 | 0.012 | 2.1 |
| 9 | LPEI-5% ClCO CH$_2$OCH$_2$COCl, NHS activation, BSAEG$_6$NH$_2$ | 7100 | 0.0052 | 0.73 | a Not Measured

The equilibrium dissociation constant ($K_d = k_{off}/k_{on}$) was 0.42 μM. The kinetic and thermodynamic parameters for the binding of CA to the mixed SAMs of the present invention that present benzene sulfonamide are comparable to those found for other, structurally similar mixed SAMs (Table 6).

A demonstration that mixed SAMs presenting benzene sulfonamide groups bind CA biospecifically can be performed with a competitive inhibition experiment. The binding of CA to this mixed SAM was completely inhibited by the addition of 1 mM benzene sulfonamide 14 (H$_2$NSO$_2$C$_6$H$_4$—CONHCH$_2$CO$_2$CH$_3$, $K_d$=63 μM) to the CA-containing solution (FIG. 14, plot A). The mixed SAM presenting 13 and —CONH(CH$_2$CH$_2$O )$_6$H)/—CO$_2$H groups also did not adsorb a detectable amount of protein when exposed to a mixture of fibrinogen, myoglobin, lysozyme, and RNase (FIG. 14, plot B); the addition of 5 μM CA to the mixture of proteins resulted in a biospecific response (FIG. 14, plot D). Mixed SAMs that presented 13 and —CONH(CH$_2$CH$_2$O)$_6$H)/—CO$_2$H groups were prepared because the longer hexa(ethylene glycol) groups reduced the nonspecific adsorption of our mixture of proteins relative to the structurally similar mixed SAM that presented 13 and —CONH(CH$_2$CH$_2$O)$_3$H)/—CO$_2$H groups (data not shown). The longer hexa(ethylene glycol) groups were more effective than the shorter tri(ethylene glycol) groups in reducing the nonspecific adsorption of proteins, probably because they are better at screening the effects of the underlying CO$_2$H/CO$_2^-$ groups.

Materials.

Carbonic anhydrase II (bovine) was purchased from Sigma (St. Louis, Mo.).

Synthesis of H$_2$N(CH$_2$CH$_2$O)$_6$CH$_2$CONH(CH$_2$)$_6$ NHCOC$_6$H$_4$SO$_2$NH$_2$ (compound 13) (FIG. 13).

{2-[2-(2-{2-[2-(2-Hydroxy-ethoxy)-ethoxy]-ethoxy}-ethoxy)-ethoxy]-ethoxy}-acetic acid tert-butyl ester (2).

To a mixture of potassium hydride (340 mg of 35% KH in mineral oil, 3.0 mmol) in dry THF (50 mL) at 0° C. was added hexa(ethylene glycol) (1.3 mL, 5.2 mmol) over 5 min. The resulting mixture was allowed to warm to ambient temperature and was stirred for 1 h. To this mixture was added tert-butyl bromoacetate (0.44 mL, 3.0 mmol) in one portion and the mixture was refluxed overnight. The reaction mixture was cooled to 0° C. and filtered to remove potassium bromide. The filtrate was concentrated in vacuo and loaded directly onto a silica gel gravity column (100 g) and eluted with CH$_2$Cl$_2$:MeOH 100:1 to 10:1 (v/v) to afford compound 2 as a clear oil (0.90 g, 44%).

{2-[2-(2-{2-[2-(2-Bromo-ethoxy)-ethoxy]-ethoxy}-ethoxy)-ethoxy]-ethoxy}-acetic acid tert-butyl ester (3).

Carbon tetrabromide (9.0 g, 27 mmol) and triphenyl phosphine (1.2 g, 4.5 mmol) were added to a solution of compound 2 (1.8 g, 4.5 mmol) in dry CH$_2$Cl$_2$ (100 mL). After stirring the reaction mixture for 5 h, the solvent was concentrated in vacuo and the residue was loaded onto a silica gel gravity column (200 g) and eluted with CH$_2$Cl$_2$: MeOH 100:0 to 20:1 (v/v) to afford compound 3 as a colorless oil (1.9 g, 91%).

{2-[2-(2-{2-[2-(2-Azido-ethoxy)-ethoxy]-ethoxy}-ethoxy)-ethoxy]-ethoxy}-acetic acid tert-butyl ester (4).

Sodium azide (1.5 g, 23 mmol) was added to a solution of compound 3 (1.9 g, 4.1 mmol) in dry DMF (50 mL) and the resulting mixture was stirred at 80° C. overnight. The reaction mixture was concentrated in vacuo and then triturated with CH$_2$Cl$_2$ (20 mL) and filtered to remove sodium azide. The filtrate was concentrated in vacuo and the residue was loaded onto a silica gel gravity column (200 g) and eluted with CH$_2$Cl$_2$:MeOH 100:0 to 20:1 (v/v) to afford compound 4 as a colorless oil (1.0 g, 57%).

Caution, sodium azide is both highly toxic and an explosive hazard; handle with care.

{2-[2-(2-{2-[2-(2-Amino-ethoxy)-ethoxy]-ethoxy}-ethoxy)-ethoxy]-ethoxy}-acetic acid tert-butyl ester (5).

To a solution of compound 4 (1.0 g, 2.4 mmol) in ethanol (20 mL) was added 10% Pd/C (0.3 g) and acetic acid (0.3 mL). The resulting mixture was stirred under an atmosphere of hydrogen for 16 hours and then filtered to remove Pd/C. The filtrate was concentrated in vacuo and the residue was loaded onto a silica gel gravity column (100 g) and eluted with CH$_2$Cl$_2$:MeOH 20:1 to 10:1 (v/v) to afford compound 5 as a oil (0.90 g, 96%).

{2-[2-(2-{2-[2-(2-Benzyloxycarbonylamino-ethoxy)-ethoxy]-ethoxy}-ethoxy)-ethoxy]-ethoxy}-acetic Acid Tert-butyl Ester (6).

Sodium hydroxide (2.0 mL of a 3M in water, 6.0 mmol) and benzoyl chloroformate (0.52 mL, 0.36 mmol) were added in portions to compound 5 (0.90 g, 2.3 mmol) in ethyl acetate (10 mL) and the resulting mixture was stirred overnight. The reaction mixture was concentrated in vacuo, water (20 mL) was added, and the slurry was extracted with $CH_2Cl_2$ (3×100 mL), and the combined organic solutions were washed with saturated aq. $NaHCO_3$ (20 mL) and brine (20 mL), and dried over anhydrous $MgSO_4$. The solution was concentrated in vacuo and the residue was loaded onto a silica gel gravity column (100 g) and eluted with $CH_2Cl_2$:MeOH 100:1 to 10:1 (v/v) to afford compound 6 as a colorless oil (0.93 g, 76%).

{2-[2-(2-{2-[2-(2-Benzyloxycarbonylamino-ethoxy)-ethoxy]-ethoxy}-ethoxy)-ethoxy]-ethoxy}-acetic acid (7).

TFA (4 mL) was added to a solution of compound 6 (0.93 g, 1.7 mmol) in $CH_2Cl_2$ (20 mL) and the resulting solution was stirred overnight at ambient temperature. The resulting solution was concentrated in vacuo and the residue was loaded onto a silica gel gravity column (50 g) and eluted with $CH_2Cl_2$:MeOH:$NH_4OH$(30% aqueous) 90:10:1 (v/v) to afford compound 7 as a thick colorless oil (0.83 g, 99%).

[[6-(2-{2-[2-(2-{2-[2-(2-Benzyloxycarbonylamino-ethoxy)-ethoxy]-ethoxy-ethoxy)-ethoxy]-ethoxy}-ethanoylamino)-hexyl]-carbamic acid tert-butyl ester (9).

To a solution of compound 7 (0.69 g, 1.5 mmol), compound 8 (0.40 g, 1.6 mmol), and TEA (0.42 mL, 3.0 mmol) in DMF (10 mL) was added 1-ethyl-3-(3-dimethylaminopropyl) carbodiimide (EDAC) (0.34 g, 1.8 mmol) and the resulting solution was stirred overnight. The reaction mixture was concentrated in vacuo, water (20 mL) was added and the slurry was extracted with $CH_2Cl_2$ (3×100 mL). The combined organic solutions were washed with saturated aq. $NaHCO_3$ (20 mL) followed by washing with brine (20 mL) then dried over anhydrous $MgSO_4$. The solution was concentrated in vacuo and the residue was loaded onto a silica gel gravity column (100 g) and eluted with $CH_2Cl_2$:MeOH 100:1 to 10:1 (v/v) to afford compound 9 as a colorless oil (0.54 g, 54%).

[2-(2-{2-[2-(2-{2-[(6-Amino-hexylcarbamoyl)-methoxy]-ethoxy}-ethoxy)-ethoxy]-ethoxy}-ethoxy)-ethyl]-carbamic acid benzyl ester (10).

TFA (3 mL) was added to a solution of compound 9 (0.24 g, 0.36 mmol) in $CH_2Cl_2$ (3 mL) and the resulting solution was stirred for 1 h at ambient temperature. The resulting solution was concentrated in vacuo and the residue was loaded onto a silica gel gravity column (25 g) and eluted with $CH_2Cl_2$:MeOH:$NH_4OH$(30% aqueous) 90:10:1 (v/v) to afford compound 10 as a colorless oil (0.20 g, 98%).

[2-(2-{2-[2-(2-{2-[(6-{1-(4-Sulfamoyl-phenyl)-methanoyl]-amino}-hexylcarbamoyl)-methoxy]-ethoxy}-ethoxy)-ethoxy]-ethoxy}-ethoxy)-ethyl]-carbamic acid benzyl ester (12).

To a solution of compound 10 (0.20 g, 0.35 mmol) and DIPEA (87 µL, 0.50 mmol) in DMF (10 mL) was added compound 11 (0.15 g, 0.50 mmol) and the resulting solution was stirred overnight. The solution was concentrated in vacuo and the residue was loaded onto a silica gel gravity column (25 g) and eluted with $CH_2Cl_2$:MeOH 10:1 (v/v) to afford compound 12 as a colorless thick oil.

Synthesis of [6-(2-{2-[2-(2-{2-[2-(2-Amino-ethoxy)-ethoxy]-ethoxy}-ethoxy)-ethoxy]-ethoxy}-ethanoylamino)-hexyl]-4-sulfamoyl-benzamide (13).

To a solution of compound 12 (0.18 g, 0.251 mmol) in ethanol (20 mL) was added 10% Pd/C (0.1 g) and the resulting mixture was stirred under an atmosphere of hydrogen for 16 hours and then filtered to remove Pd/C. The filtrate was concentrated in vacuo and the residue was purified by HPLC to afford compound 13 as waxy solid.

Immobilization of Biospecific Ligands on Polymer Surfaces.

A biospecific surface can be prepared by the covalent immobilization of a benzene sulfonamide derivative to a surface functionalized with LPEI (Table 6); carbonic anhydrase binds to this surface in a biospecific manner. The benzenesulfonamide derivative was immobilized on inert surface coatings using the following procedures. The polyamine (PEI) was grafted to the surface that presents interchain carboxylic anhydride groups using the method described in Example 3. This PEI substrate was immersed in a solution triethylamine (300 µL), a catalytic amount of dimethylaminopyridine, acetyl chloride (10 mM), and diglycoyl chloride (0.1 or 0.5 mM) in $CH_2Cl_2$ (10 mL) for 1 h. The presence of difunctional acid chloride (diglycoyl chloride) introduces reactive functional groups that allow for covalent attachment of the analyte of interest in a subsequent step. Two procedures for attaching a ligand to the surface are described. They are only representative examples since those skilled in the art would know how to modify existing immobilization chemistries to the polyamine surface described herein.

In one method, the residual acid chloride groups of the acetylated substrates were hydrolyzed to carboxylic acid groups by immersion in a solution of PBS for 20 min. Thecarboxylic acid groups on these substrates were then activated to NHS esters by methods commonly known by those skilled in the art. Covalent attachment of the analyte (benzene sulfonamide derivative) to this surface was achieved by the reaction of the amino group terminus of this analyte with the activated NHS ester on the surface of the substrate. This reaction was carried out in a 10 mM solution of the analyte in NMP for 30 min at room temperature.

In another method, the residual acid chloride groups of the acetylated substrates were reacted with a solution of diamine (hexaethyleneglycol diamine, 10 mM), and triethylamine (20 mM) in methylene chloride (10 mL). These substrates that present amino groups were then reacted with a benzene sulfonamide derivative that contained an activated NHS ester (20 mM) in 1:1 sodium borate buffer:NMP, in the presence of catalytic amount of DMAP.

Figure 16:
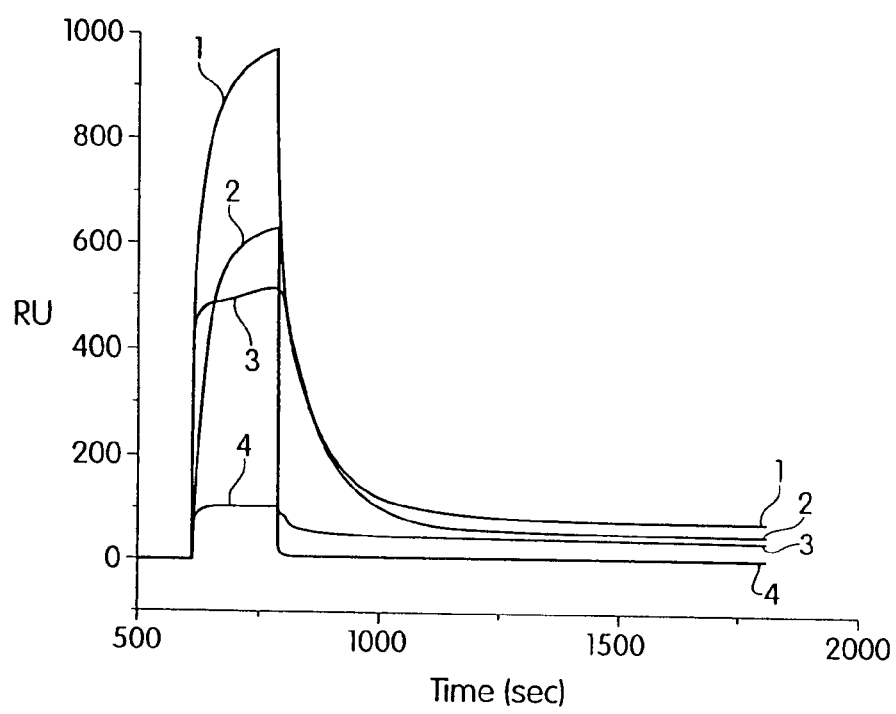
FIG. 16 shows SPR sensorgrams for the adsorption of CA to a thin film of LPEI that was grafted on a SAM terminated with anhydride groups.

FIG. 16 shows SPR sensorgrams for the adsorption of proteins to a thin film of LPEI that was grafted on a SAM terminated with anhydride groups. This PEI substrate was immersed in a solution triethylamine (300 µL), a catalytic amount of dimethylaminopyridine, acetyl chloride (10 mM), and diglycoyl chloride (0.1 mM) in $CH_2Cl_2$ (10 mL) for 1 h. The residual acid chloride groups of the acetylated substrates were allowed to react with a solution of diamine (hexaethyleneglycol diamine, 10 mM), and triethylamine (20 mM) in methylene chloride (10 mL). These substrates that present amino groups were then allowed to react with a benzene sulfonamide derivative that contained an activated NHS ester (20 mM) in 1:1 borate buffer:NMP, in the presence of catalytic amount of DMAP. Curve 1: CA (5 µM) with a mixture of proteins (each at 0.2 mg/mL) including fibrinogen, RNase, lysozyme, and myoglobin; Curve 2: CA (5 µM); Curve 3: a mixture of proteins as in 1 without CA; Curve 4: CA (5 µM) with 1 mM soluble benzenesulfonamide ligand. The kinetic parameters obtained from these sensorgrams are in entry 6 of Table 6.

Those skilled in the art would readily appreciate that all parameters listed herein are meant to be examples and that actual parameters will depend upon the specific application for which the methods and apparatus of the present invention are used. It is, therefore, to be understood that the foregoing embodiments are presented by way of example only and that, within the scope of the appended claims and equivalents thereto, the invention may be practiced otherwise than as specifically described.

What is claimed:

1. An article, comprising:
a substrate having covalently bonded thereon a chemical chain, the chemical chain comprising a terminal group comprising the structure:

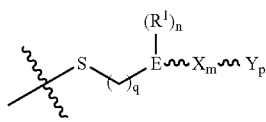

wherein the terminal group is hydrophilic; E is selected from the group consisting of nitrogen, oxygen, phosphorus and sulfur; X is an organic substituent and m is an integer less than or equal to 3; Y is selected from the group consisting of amides, amide derivatives, amines, amine derivatives, cyclic ethers, sugar derivatives, amino acids, amino acid derivatives, and multiple nitriles and p is an integer greater than 0; X and Y are both free of a hydrogen-bond donor; $R^1$ is selected from the group consisting of hydrogen, a $C_1$-$C_6$ alkyl and an aryl, and n is an integer less than or equal to 2; ∿∿∿ represents one or more single bonds, a double bond, or any combination thereof; q is an integer greater than 0; optionally $R^1$ can bond to X or Y to form a cyclic structure; the chemical chain further comprising a linker covalently bonded to the terminal group and to the substrate; and the article being resistant to the adsorption of proteins, cells or bacteria.

2. An article, comprising:
a substrate having covalently bonded thereon a chemical chain, the chain comprising a terminal group comprising the structure:

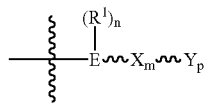

wherein the terminal group is hydrophilic; E is selected from the group consisting of nitrogen, oxygen, phosphorus and sulfur; X is an organic substituent and m is an integer less than or equal to 3; Y is selected from the group consisting of amides, amide derivatives, amines, amine derivatives, cyclic ethers, sugar derivatives, amino acids, amino acid derivatives, and multiple nitriles and p is an integer greater than 0; X and Y are both free of a hydrogen-bond donor; $R^1$ is selected from the group consisting of hydrogen, a $C_1$-$C_6$ alkyl and an aryl, and n is an integer less than or equal to 2; ∿∿∿ represents one or more single bonds, a double bond, or any combination thereof; optionally $R^1$ can bond to X or Y to form a cyclic structure; the chemical chain comprising a linker covalently bonded to the terminal group and to the substrate; the linker comprising the structure:

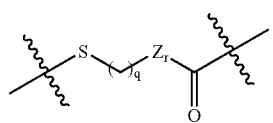

wherein q is an integer greater than 0, Z comprises a heteroatom, and r is equal to 0 or 1; and the article being resistant to the adsorption of proteins, cells or bacteria.

3. The article of claim 2, wherein E is nitrogen.

4. The article of claim 2, wherein the terminal group has an overall neutral charge.

5. The article of claim 4, wherein the chemical chain has an overall neutral charge.

6. The article of claim 2, wherein a terminal group of the chain is charged and neutralized by at least one neighboring terminal group of an opposite charge.

7. The article of claim 2, wherein the article comprises a monolayer of a plurality of chemical chains bonded to the substrate.

8. The article of claim 7, wherein the monolayer is a self-assembled monolayer.

9. The article of claim 7, wherein the chemical chain is a first chemical chain and the monolayer further comprises a second chemical chain having a different composition from the first chemical chain, the second chemical chain being present in an amount of less than about 75% of a total of the chemical chains in the monolayer.

10. The article of claim 9, wherein the second chemical chain is present in an amount of less than about 50% of the total of the chemical chains in the monolayer.

11. The article of claim 9, wherein the second chemical chain is present in an amount of less than about 25% of the total of the chemical chains in the monolayer.

12. The article of claim 9, wherein the second chemical chain comprises a terminal group selected from the group consisting of a $C_1$-$C_{25}$ alkyl, an aryl, a carboxylic acid, a thiol, a hydroxyl and a quaternary ammonium ion.

13. The article of claim 9, wherein the second chemical chain comprises a terminal group comprising the structure:

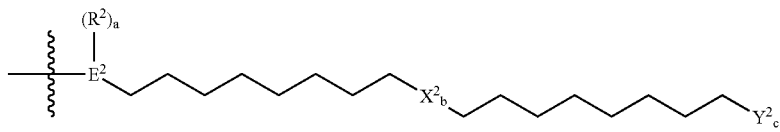

wherein the terminal group is hydrophilic; $E^2$ is selected from the group consisting of nitrogen, oxygen, phosphorus and sulfur; $X^2$ is an organic substituent and b is an integer less than or equal to 3; $Y^2$ is selected from the group consisting of amides, amide derivatives, amines, amine derivatives, cyclic ethers, sugar derivatives, amino acids, amino acid derivatives, and multiple nitriles and c is an integer greater than 0; $X^2$ and $Y^2$ are both free of a hydrogen-bond donor; $R^2$ is selected from the group consisting of hydrogen, a $C_1$-$C_6$ alkyl and an aryl, and a is an integer less than or equal to 2; ⋀⋀⋀represents one or more single bonds, a double bond, or any combination thereof; optionally $R^2$ can bond to $X^2$ or $Y^2$ to form a cyclic structure.

14. The article of claim 9, wherein the second chemical chain has a smaller average length than an average length of the first chemical chain.

15. The article of claim 2, wherein the chemical chain comprises a straight-chain backbone.

16. The article of claim 2, wherein Z is selected from the group consisting of oxygen, nitrogen, silicon and sulfur.

17. The article of claim 2, wherein the chemical chain comprises the structure:

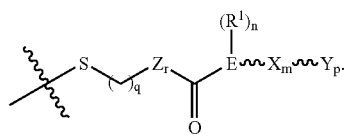

18. The article of claim 17, wherein Z is selected from the group consisting of oxygen, nitrogen, silicon and sulfur.

19. The article of claim 17, wherein q is greater than 3.

20. The article of claim 2, wherein the substrate comprises a first composition and the chemical chain comprises a second composition different from the first composition.

21. The article of claim 20, wherein the substrate comprises a material selected from the group consisting of a metal, a ceramic and a polymer.

22. The article of claim 21, wherein the substrate is gold.

23. The article of claim 21, wherein the substrate is silica.

24. The article of claim 2, wherein the terminal group includes hydrogen-bond acceptor groups.

25. The article of claim 2, wherein the article is resistant to the adsorption proteins such that the article adsorbs no more than 60% of a monolayer of proteins.

26. The article of claim 2, wherein the article is resistant to the adsorption proteins such that the article adsorbs no more than 50% of a monolayer of proteins.

27. The article of claim 2, wherein the article is resistant to the adsorption proteins such that the article adsorbs no more than 30% of a monolayer of proteins.

28. The article of claim 2, wherein Y comprises the structure:

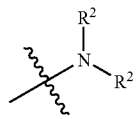

wherein $R^2$ is a $C_1$-$C_6$ alkyl.

29. An article, comprising:
a substrate having covalently bonded thereon a chemical chain, wherein the chemical chain comprises a hydrophilic terminal group comprising the structure:

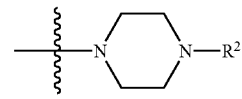

wherein $R^2$ is selected from the group consisting of a $C_1$-$C_6$ alkyl, an ether, an ether derivative, an ester, a formyl, a carboxyl, and $C(O)R^3$ in which $R^3$ is a $C_1$-$C_6$ alkyl; and the article being resistant to the adsorption of proteins, cells or bacteria.

30. An article, comprising:
a substrate having covalently bonded thereon a chemical chain, the chain comprising a terminal group comprising the structure:

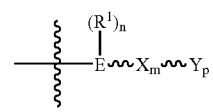

wherein the terminal group is hydrophilic; E is selected from the group consisting of nitrogen, oxygen, phosphorus and sulfur; X is an organic substituent and m is an integer less than or equal to 3; p is an integer greater than 0; X and Y are both free of a hydrogen-bond donor; $R^1$ is selected from the group consisting of hydrogen, a $C_1$-$C_6$ alkyl and an aryl, and n is an integer less than or equal to 2; ⋀⋀⋀represents one or more single bonds, a double bond, or any combination thereof; optionally $R^1$ can bond to X to form a cyclic structure; the article being resistant to the adsorption of proteins, cells or bacteria; and wherein Y is selected from the group consisting of an amide comprising the structure:

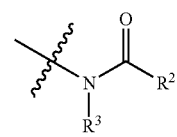

wherein $R^2$ and $R^3$ are the same or different and each is a $C_1$-$C_6$ alkyl and an amide comprising the structure:

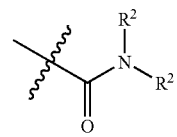

wherein each $R^2$ is the same or different and each is a $C_1$-$C_6$ alkyl.

31. The article of claim 30, wherein the terminal group comprises the structure:

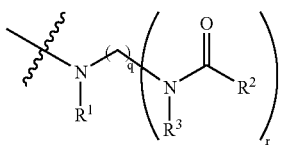

wherein $R^2$ comprises a terminal or linking $C_1$-$C_6$ alkyl, and each of q and r is an integer greater than 0.

32. The article of claim 30, wherein the terminal group comprises the structure:

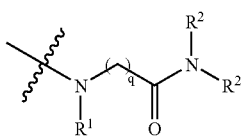

wherein q is an integer greater than 0.

33. The article of claim 30, wherein the terminal group comprises the structure:

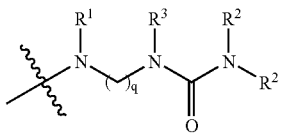

wherein $R^3$ is a $C_1$-$C_3$ alkyl and q is an integer greater than 0.

34. An article, comprising:
a substrate having covalently bonded thereon a chemical chain, the chain comprising a terminal group comprising the structure:

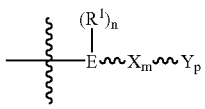

wherein the terminal group is hydrophilic; E is selected from the group consisting of nitrogen, oxygen, phosphorus and sulfur; X is an organic substituent and m is an integer less than or equal to 3; Y comprises a structure selected from the group consisting of:

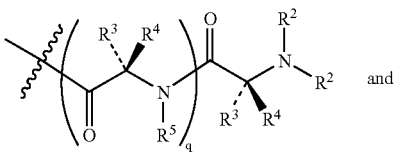 and

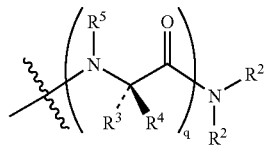

wherein the group enclosed within parenthesis represents an amino acid or an amino acid derivative, $R^2$ is a $C_1$-$C_6$ alkyl, $R^3$, $R^4$ and $R^5$ can be the same or different and each is an organic group, q is an integer greater than one, and p is an integer greater than 0; X and Y are both free of a hydrogen-bond donor; $R^1$ is selected from the group consisting of hydrogen, a $C_1$-$C_6$ alkyl and an aryl, and n is an integer less than or equal to 2; ⋀⋀⋀ represents one or more single bonds, a double bond, or any combination thereof; optionally $R^1$ can bond to X to form a cyclic structure; and the article being resistant to the adsorption of proteins, cells or bacteria.

35. The article of claim 34, wherein $R^2$ is an alkyl selected from the group consisting of methyl and ethyl.

36. The article of claim 34, wherein the amino acid is glycine.

37. The article of claim 34, wherein the amino acid derivative comprises an N-alkyl amino acid alkylated with a $C_1$-$C_6$ alkyl.

38. The article of claim 37, wherein the amino acid derivative is N-methyl glycine.

39. An article, comprising:
a substrate having covalently bonded thereon a chemical chain, wherein the chemical chain comprises a hydrophilic terminal group comprising the structure:

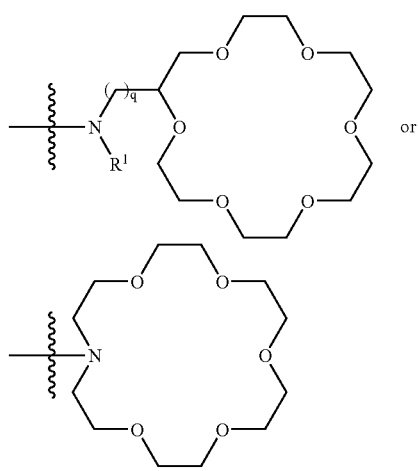

wherein $R^1$ is a $C_1$-$C_6$ alkyl and q is an integer greater than or equal to 0; and the article being resistant to the adsorption of proteins, cells or bacteria.

40. An article, comprising:
a substrate having covalently bonded thereon a chemical chain, the chain comprising a terminal group comprising the structure:

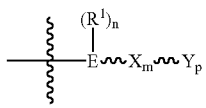

wherein the terminal group is hydrophilic; E is selected from the group consisting of nitrogen, oxygen, phosphorus and sulfur; X is an organic substituent and m is an integer less than or equal to 3; Y comprises a sugar derivative peralkylated with a $C_1$-$C_6$ alkyl and p is an integer greater than 0; X and Y are both free of a hydrogen-bond donor; $R^1$ is selected from the group consisting of hydrogen, a $C_1$-$C_6$ alkyl and an aryl, and n is an integer less than or equal to 2; ⋀⋀⋀represents one or more single bonds, a double bond, or any combination thereof; optionally $R^1$ can bond to X or Y to form a cyclic structure; and the article being resistant to the adsorption of proteins, cells or bacteria.

41. The article of claim 40, wherein the terminal group comprises the structure:

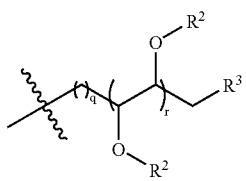

wherein $R^2$ and $R^3$ are the same or different and each is a $C_1$-$C_6$ alkyl, q and r are the same or different and each is an integer greater than 0.

42. An article, comprising:
a substrate having covalently bonded thereon a chemical chain, the chain comprising a terminal group comprising the structure:

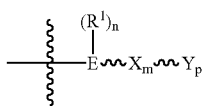

wherein the terminal group is hydrophilic; E is selected from the group consisting of nitrogen, oxygen, phosphorus and sulfur; X is an organic substituent and m is an intege less than or equal to 3; Y is a multiple nitrile comprising the structure —{$(CH_2)q$—$CN$}$_2$, wherein q is greater than 0 and p is an integer greater than 0; X and Y are both free of a hydrogen-bond donor; $R^1$ is selected from the group consisting of hydrogen, a $C_1$-$C_6$ alkyl and an aryl, and n is an integer less than or equal to 2; ⋀⋀⋀represents one or more single bonds, a double bond, or any combination thereof; optionally $R^1$ can bond to X or Y to form a cyclic structure; and the article being resistant to the adsorption of proteins, cells or bacteria.

43. The article of claim 42, wherein the terminal group comprises the structure:

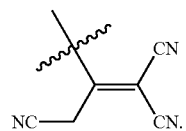

44. An article comprising a substrate having a chemical group covalently bonded thereon, the chemical group being selected from the group consisting of:

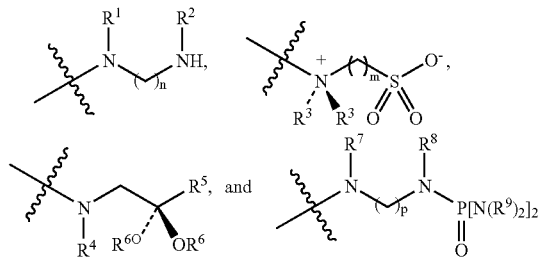

wherein $R^1$, $R^4$ and $R^7$ are the same or different and each is selected from the group consisting of hydrogen and a $C_1$-$C_6$ alkyl; $R^3$, $R^5$, $R^7$, $R^8$ and $R^9$ are the same or different and each is a $C_1$-$C_6$ alkyl; $R^6$ is a $C_1$-$C_6$ alkyl; and m, n and p are the same or different and each is an integer greater than 0, the article being resistant to the adsorption of proteins, cells or bacteria.

45. The article of claim 44, wherein each of $R^1$, $R^4$, $R^6$, $R^7$, $R^8$ and $R^9$ is a methyl.

* * * * *